(12) United States Patent
Mine et al.

(10) Patent No.: US 11,103,214 B2
(45) Date of Patent: Aug. 31, 2021

(54) ULTRASONIC DIAGNOSTIC APPARATUS USING SYNTHETIC AND MOVING APERTURE SYNTHESIS

(71) Applicant: TOSHIBA MEDICAL SYSTEMS CORPORATION, Otawara (JP)

(72) Inventors: Yoshitaka Mine, Nasushiobara (JP); Kazutoshi Sadamitsu, Otawara (JP); Masami Takahashi, Nasushiobara (JP); Masatoshi Nishino, Otawara (JP); Norihisa Kikuchi, Otawara (JP); Naoyuki Nakazawa, Otawara (JP); Atsushi Nakai, Nasushiobara (JP); Jiro Higuchi, Otawara (JP); Yutaka Kobayashi, Nasushiobara (JP); Cong Yao, Otawara (JP); Kazuo Tezuka, Nasushiobara (JP); Naoki Yoneyama, Yaita (JP); Atsushi Sumi, Otawara (JP)

(73) Assignee: TOSHIBA MEDICAL SYSTEMS CORPORATION, Otawara (JP)

( * ) Notice: Subject to any disclaimer, the term of this patent is extended or adjusted under 35 U.S.C. 154(b) by 412 days.

(21) Appl. No.: 15/450,886

(22) Filed: Mar. 6, 2017

(65) Prior Publication Data
US 2017/0252007 A1    Sep. 7, 2017

(30) Foreign Application Priority Data

Mar. 7, 2016    (JP) .............................. JP2016-043829
Feb. 8, 2017    (JP) .............................. JP2017-021035

(51) Int. Cl.
*A61B 8/00*     (2006.01)
*A61B 8/08*     (2006.01)
*G01S 15/89*    (2006.01)

(52) U.S. Cl.
CPC .......... *A61B 8/4461* (2013.01); *A61B 8/4218* (2013.01); *A61B 8/4483* (2013.01); *A61B 8/5207* (2013.01); *G01S 15/8925* (2013.01); *G01S 15/8927* (2013.01); *G01S 15/8945* (2013.01); *G01S 15/8995* (2013.01); *G01S 15/8997* (2013.01); *G01S 15/8993* (2013.01)

(58) Field of Classification Search
None
See application file for complete search history.

(56) References Cited

U.S. PATENT DOCUMENTS 6,464,638 B1 *  10/2002  Adams ................. A61B 8/5253
                                                           600/443
2003/0163046 A1 *  8/2003  Nohara ............... G01S 15/8993
                                                           600/443

(Continued)

FOREIGN PATENT DOCUMENTS

JP    10-179579    7/1998
JP    2009-240700  10/2009

(Continued)

OTHER PUBLICATIONS

Japanese Office Action dated Oct. 28, 2020, issued in Japanese Patent Application No. 2017-021035.

*Primary Examiner* — Serkan Akar
*Assistant Examiner* — Aminah Asghar
(74) *Attorney, Agent, or Firm* — Oblon, McClelland, Maier & Neustadt, L.L.P.

(57) ABSTRACT

In one embodiment, an ultrasonic diagnostic apparatus includes a probe configured to be equipped with plural transducers arranged in a first direction and a second direction perpendicular to the first direction and be able to perform a two-dimensional scan in the first and second directions; a moving device configured to support the probe and mechanically move the probe in the second direction; a (Continued)

receiving circuit configured to generate first reception signals for respective moving positions of the probe in the second direction by performing receiving phase-compensation and summation processing on respective reflected signals received by the plurality of transducers at each of the moving positions; and processing circuitry configured to generate a second reception signal by performing moving aperture synthesis on the first reception signals generated for the respective moving positions of the probe based on positional information of the probe and generate image data from the second reception signal.

11 Claims, 22 Drawing Sheets

(56) References Cited

U.S. PATENT DOCUMENTS

| | | |
|---|---|---|
| 2009/0326377 A1 | 12/2009 | Hirama |
| 2010/0191111 A1* | 7/2010 | Azuma .................... A61B 8/08 600/438 |
| 2012/0044785 A1* | 2/2012 | Yoda .................... G01S 7/52046 367/92 |
| 2013/0308850 A1* | 11/2013 | Oikawa ............... G01S 7/52085 382/131 |
| 2015/0223782 A1* | 8/2015 | Yamagata ............ A61B 8/5292 600/462 |
| 2015/0359512 A1* | 12/2015 | Boctor ................ G01S 15/8997 600/444 |
| 2017/0150947 A1* | 6/2017 | Yoshizawa ............... A61B 8/00 |

FOREIGN PATENT DOCUMENTS

| | | |
|---|---|---|
| JP | 2010-82333 | 4/2010 |
| JP | 2010-269046 A | 12/2010 |
| JP | 2011-182978 | 9/2011 |
| JP | 2012-55346 | 3/2012 |
| JP | 2012-161563 A | 8/2012 |
| JP | 2016-002281 A | 1/2016 |

* cited by examiner

ARRANGEMENT OF TRANCEDUCERS OF 2DA PROBE

MECHANICHAL MOVEMENT OF 2DA PROBE IN SLICE DIRECTION

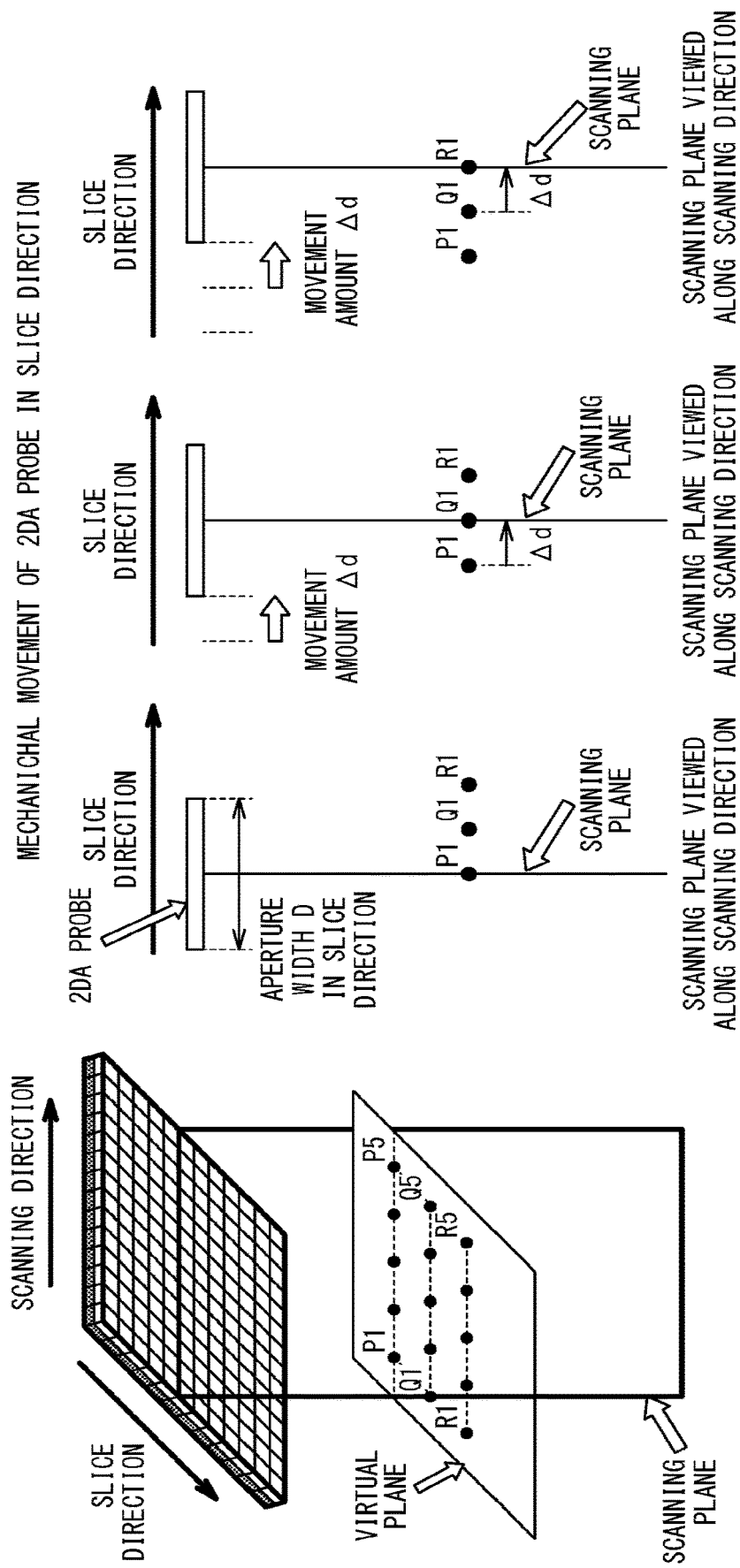

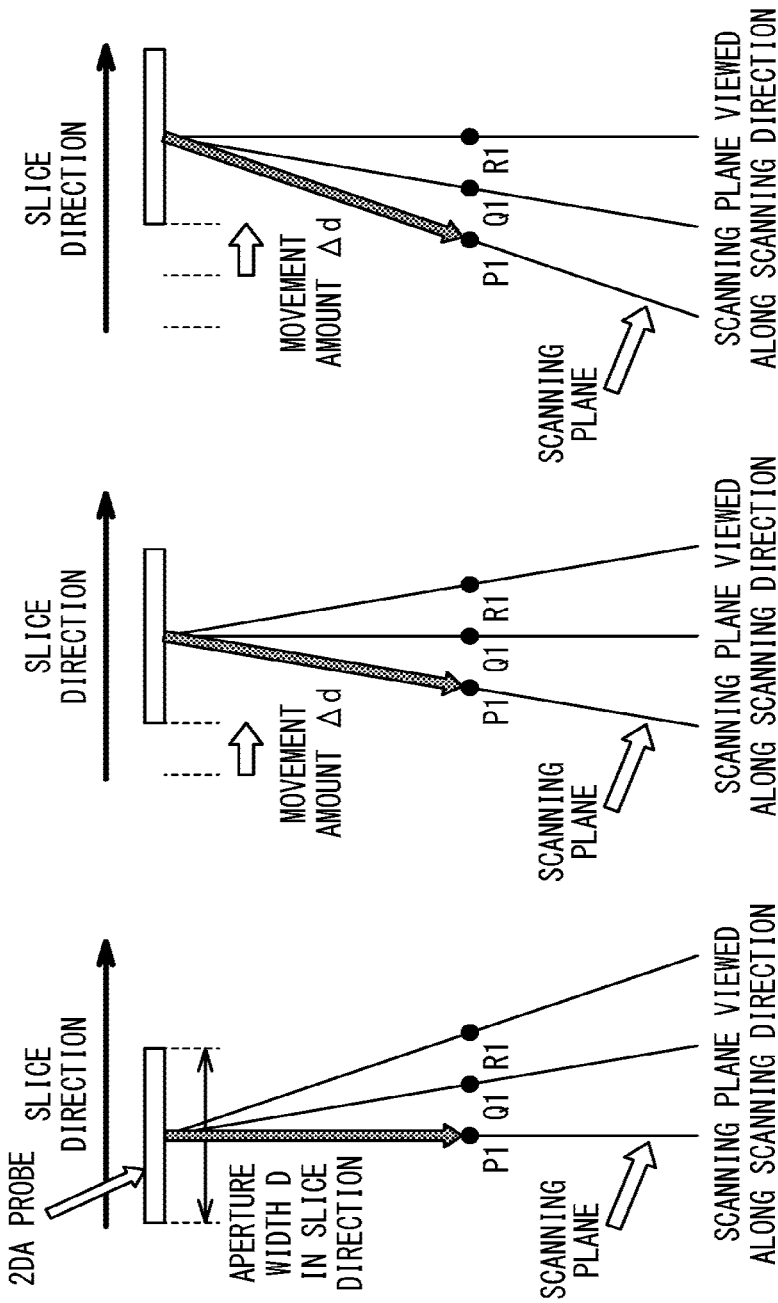

MECHANICAL MOVEMENT IN SLICE DIRECTION AND APERTURE SYNTHESIS PROCESSING

SPATIAL-COMPOUND PROCESSING IN SCANNING DIRECTION AND SLICE DIRECTION

ULTRASONIC DIAGNOSTIC APPARATUS USING SYNTHETIC AND MOVING APERTURE SYNTHESIS

CROSS-REFERENCE TO RELATED APPLICATIONS

This application is based upon and claims the benefit of priority from Japanese Patent Application No. 2016-043829, filed on Mar. 7, 2016 and Japanese Patent Application No. 2017-021035 filed on Feb. 8, 2017, the entire contents of each of which are incorporated herein by reference.

FIELD

Embodiments described herein relate generally to an ultrasonic diagnostic apparatus.

BACKGROUND

An ultrasonic diagnostic apparatus is configured to non-invasively acquire information inside an object such as a patient by transmitting an ultrasonic pulse and/or an ultrasonic continuous wave generated by transducers included in an ultrasonic probe into the object's body and converting a reflected ultrasonic wave caused by difference in acoustic impedance between respective tissues inside the object into an electric signal. In a medical examination using an ultrasonic diagnostic apparatus, various types of moving image data and/or real-time image data can be easily acquired by scanning an object such that an ultrasonic probe is brought into contact with a body surface of the object. Thus, an ultrasonic diagnostic apparatus is widely used for morphological diagnosis and functional diagnosis of an organ.

Additionally, a three-dimensional ultrasonic diagnostic apparatus is known, which is equipped with a one-dimensional array probe configured to mechanically swing or rotate, or equipped with a two-dimensional array probe, for acquiring three-dimensional image data. Further, a four-dimensional ultrasonic diagnostic apparatus configured to time-sequentially acquire three-dimensional image data substantially on a real-time basis is also known.

Moreover, an ultrasonic diagnostic apparatus equipped with a robot arm configured to hold and move an ultrasonic probe by programming a body-surface scanning procedure of a skilled operator is proposed as an attempt to shorten an examination time.

In the case of acquiring a three-dimensional image by mechanically fluctuating or moving a one-dimensional array probe, it is difficult to obtain a three-dimensional image with satisfactory image quality, because an aperture of the one-dimensional array probe in the slice direction is small. Additionally, its narrow scanning range is also a factor of reducing practical use of a one-dimensional array probe.

Although a three-dimensional image can be acquired by electronically scanning an ultrasonic beam in two directions with the use of a two-dimensional array probe, a two-dimensional array probe is square-shaped, which makes it hard to fit a body surface.

Further, in consideration of imaging from between ribs, it is required to reduce an aperture size in the slice direction to the degree equivalent to a one-dimensional array probe. If the aperture size of the two-dimensional array probe is reduced to such a degree, similarly to a one dimensional probe, it is difficult to acquire a three-dimensional image with satisfactory image quality due to its small aperture in the slice direction.

For these reasons, an ultrasonic diagnostic apparatus which can stably acquire a three-dimensional image with high image quality and high resolution over a wide scanning range has been desired.

BRIEF DESCRIPTION OF THE DRAWINGS

In the accompanying drawings:

FIG. 11A to FIG. 11D are schematic diagrams also illustrating the method of mechanically moving of a 2DA probe in the slice direction;

FIG. 12A to FIG. 12C are schematic diagrams illustrating a concept of mechanical movement of a 2DA probe and beam formation;

DETAILED DESCRIPTION

Hereinafter, embodiments of the present invention will be described with reference to the accompanying drawings.

In one embodiment, an ultrasonic diagnostic apparatus includes a probe configured to be equipped with a plurality of transducers arranged in a first direction and a second direction perpendicular to the first direction and be able to perform a two-dimensional scan in the first direction and the second direction; a moving device configured to support the probe and mechanically move the probe in the second direction; a receiving circuit configured to generate first reception signals for respective moving positions of the probe in the second direction by performing receiving phase-compensation and summation processing on respective reflected signals received by the plurality of transducers at each of the moving positions; and processing circuitry configured to generate a second reception signal by performing moving aperture synthesis on the first reception signals generated for the respective moving positions of the probe based on positional information of the probe and generate image data from the second reception signal.

(General Configuration)

Figure 1:
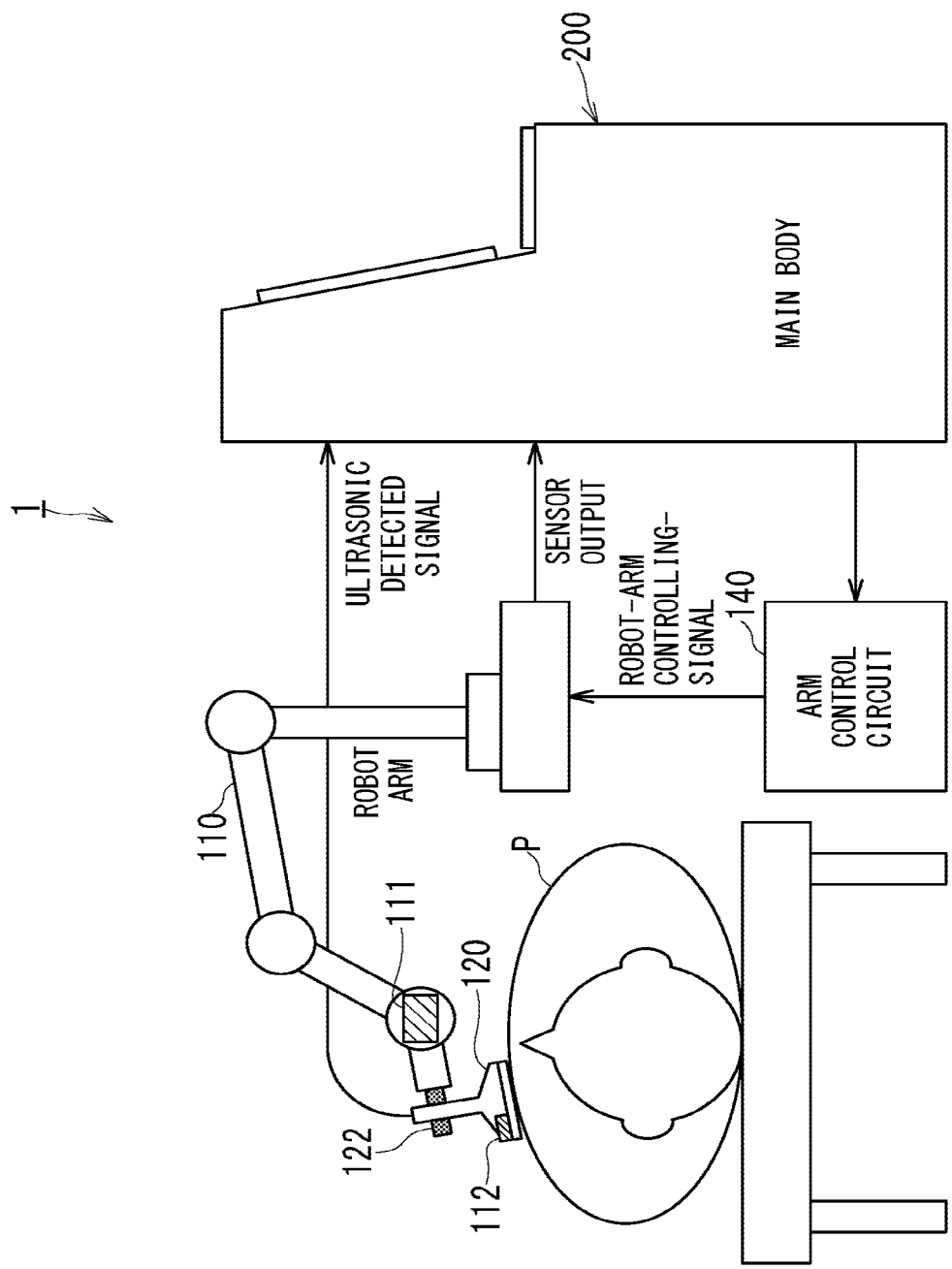
FIG. 1 is a block diagram illustrating general configuration of the ultrasonic diagnostic apparatus of the present embodiment.

FIG. 1 is a block diagram illustrating general configuration of the ultrasonic diagnostic apparatus 1 of the present embodiment. The ultrasonic diagnostic apparatus 1 includes at least a main body 200 of the apparatus (hereinafter, simply referred to as the main body 200), an ultrasonic probe 120, a robot arm 110, and a robot arm controller 140. The robot arm 110 is an instance of a moving device configured to mechanically move the ultrasonic probe 120.

The robot arm 110 holds (i.e., supports) the ultrasonic probe 120 by, e.g., its end, and can move the ultrasonic probe 120 with six degrees of freedom according to a control signal inputted from the robot arm controller 140. To be able to move the ultrasonic probe 120 with six degrees of freedom means, e.g., to be able to move it at arbitrary combination of six components including three translation direction components (X, Y, Z) and three rotational direction components (θx, θy, θz). The above-described three translation direction components (X, Y, Z) correspond to an X-axis direction, a Y-axis direction, and a Z-axis direction perpendicular to each other. The above-described three rotational directions correspond to rotation about the X-axis, rotation about the Y-axis, and rotation about the Z-axis. In other words, the robot arm 110 can locate the ultrasonic probe 120 at a desired position and at a desired orientation in three-dimensional space, and can move the ultrasonic probe 120 along a desired path at a desired velocity.

The robot arm 110 is provided with an arm sensor 111, and detects motions of respective parts of the robot arm 110 by the arm sensor 111. At least a position sensor is included in the arm sensor 111 of the robot arm 110, and the robot arm 110 detects the above-described six components by using this position sensor. Additionally, a velocity sensor may be included in the arm sensor 111 of the robot arm 110 in addition to the position sensor. Further, an acceleration sensor may be included in the arm sensor 111 of the robot arm 110 in addition to the position sensor and the velocity sensor.

Moreover, the arm sensor 111 of the robot arm 110 preferably includes a pressure sensor. Biological contact pressure of the ultrasonic probe 120 is transmitted to the robot arm 110 via an ultrasonic probe adapter (supporting member) 122, and is detected by the pressure sensor included in the robot arm 110.

Additionally or alternatively to the above-described arm sensor 111, one or more probe sensor 112 such as a pressure sensor, a position sensor, a velocity sensor, and/or an acceleration sensor may be mounted on the ultrasonic probe 120.

Respective detection signals of the position sensor and the pressure sensor and/or respective detection signals of the velocity sensor and the acceleration sensor are used for feedback control performed by the robot arm controller 140. The robot arm 110 is driven by the robot arm controller 140 according to predetermined trace information. The trace information is information defining a trace of the ultrasonic probe 120 such as a position, orientation, a moving path, a moving velocity, and biological contact pressure. The robot arm controller 140 performs feedback control of the robot arm 110 by using this trace information and detection signals of the respective sensors of the arm sensor 111 in such a manner that the ultrasonic probe 120 moves according to this trace information.

As described above, the robot arm 110 can automatically move the ultrasonic probe 120 along a body surface of the object (i.e., target examinee) P according to the trace information under the control of the robot arm controller 140.

Additionally, a user can manually move the ultrasonic probe 120 under a condition where the ultrasonic probe 120 is held by the robot arm 110, instead of the above automatic control. In this case, the robot arm 110 is separated from the robot arm controller 140 and moves according to an operator's manipulation of the ultrasonic probe 120. Also in this case, the arm sensor 111 including, e.g., the position sensor and/or the pressure sensor mounted on the robot arm 110 continues to operate such that the detection signals detected by the arm sensor 111 and indicative of, e.g., position, velocity, acceleration, and biological contact pressure are sequentially transmitted to the main body 200.

Figure 2:
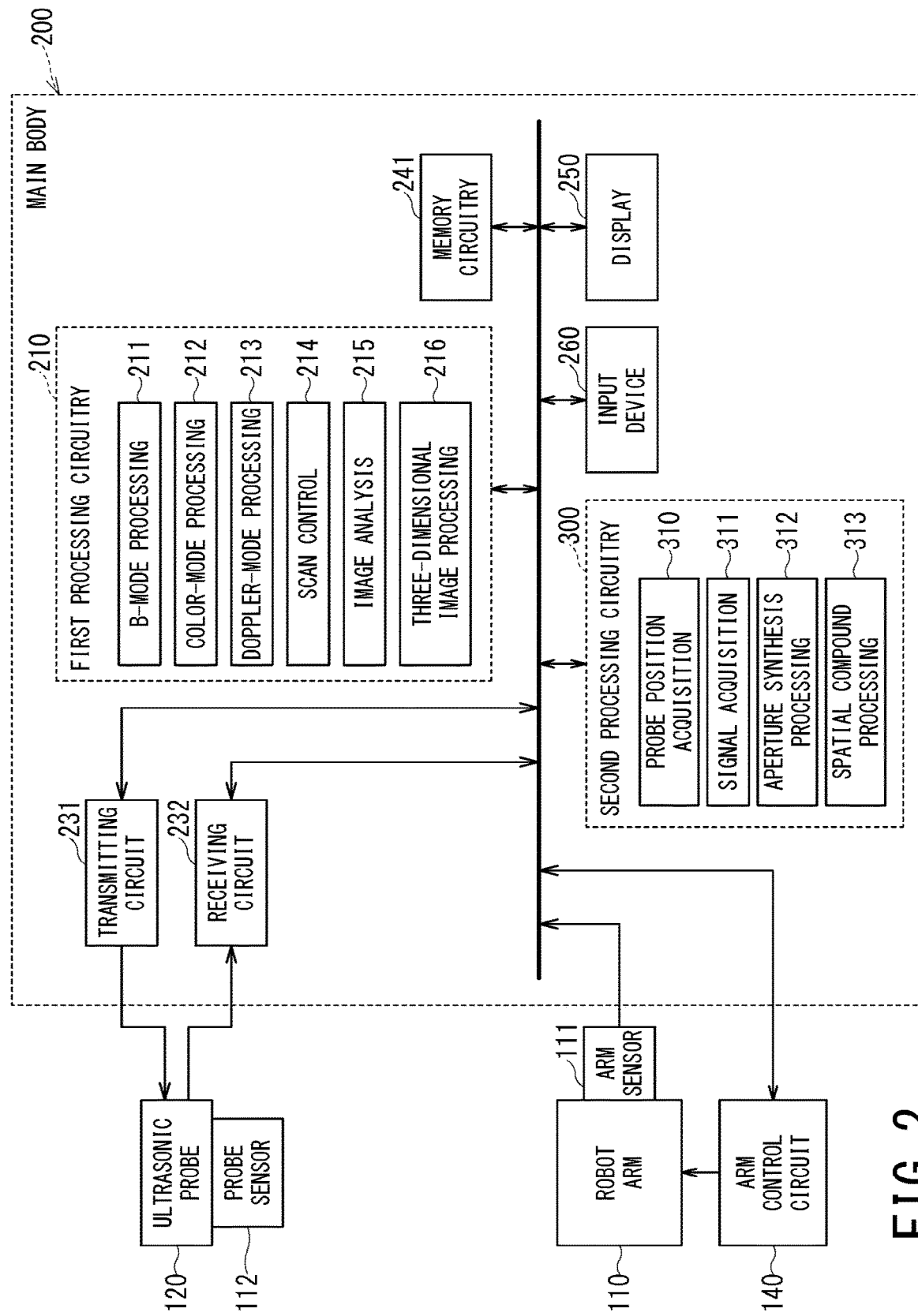
FIG. 2 is a block diagram illustrating detailed configuration of the ultrasonic diagnostic apparatus of the present embodiment.

FIG. 2 is a block diagram illustrating detailed configuration of the ultrasonic diagnostic apparatus 1, especially illustrating detailed configuration of its main body 200.

As described in FIG. 1, the main body 200 is connected to the ultrasonic probe 120, the robot arm 110, the arm sensor 111, and the robot arm controller 140 (hereinafter, referred to as the arm control circuit 140 according to the notation in FIG. 2). Aside from those components, an ECG/respiration sensor 180 can also be connected to the main body 200.

The main body 200 includes a transmitting circuit 231, a receiving circuit 232, first processing circuitry 210, memory circuitry 241, a display 250, an input device 260, and second processing circuitry 300.

The transmitting circuit 231 includes circuit components such as a trigger generation circuit, a delay circuit, and a pulsar circuit, and supplies a driving signal to the ultrasonic probe 120. The trigger generation circuit repetitively generates rate pulses at a predetermined frequency. The delay circuit delays each of the rate pulses by a predetermined delay amount for each transducer of the ultrasonic probe 120. The delay circuit is a circuit for focusing a transmission beam or directing a transmission beam in a desired direction. The pulsar circuit generates a pulse signal based on the delayed rate pulses, and applies the pulse signal to the respective transducers of the ultrasonic probe 120.

The ultrasonic probe 120 transmits an ultrasonic signal to an object and receives the reflected ultrasonic signal from inside of the object. The ultrasonic probe 120 may be a one-dimensional array probe or a two-dimensional array probe. As described below, the ultrasonic probe 120 may be a 1.25-dimensional array probe, a 1.5-dimensional array probe, or a 1.75-dimensional array probe. The ultrasonic signal received by the ultrasonic probe 120 is converted into an electric signal by each of the transducers and supplied to the receiving circuit 232.

The receiving circuit 232 includes circuit components such as amplifier circuits, analog to digital (A/D) conversion circuits, and a receiving phase-compensation/summation circuit 234. In the receiving circuit 232, each of the amplifier circuits amplifies each received analogue signal supplied from the respective transducers of the ultrasonic probe 120, and then each of the A/D conversion circuits converts the respective received analogue signals into digital signals. Afterward, the receiving phase-compensation/summation circuit 234 performs a receiving phase-compensation and summation processing. That is, the receiving phase-compensation/summation circuit 234 separately compensates the respective phases of the digital signals outputted from the respective A/D conversion circuits by adding a delay amount to each of the digital signals, and then generates a reception signal corresponding to a desired beam direction by summing up those digital signals. Note that a beam formed by the receiving phase-compensation/summation circuit 234 of the receiving circuit 232 is a beam in the arrangement direction of the transducers inside the ultrasonic probe 120, i.e., a beam in the azimuth direction.

Figure 3:
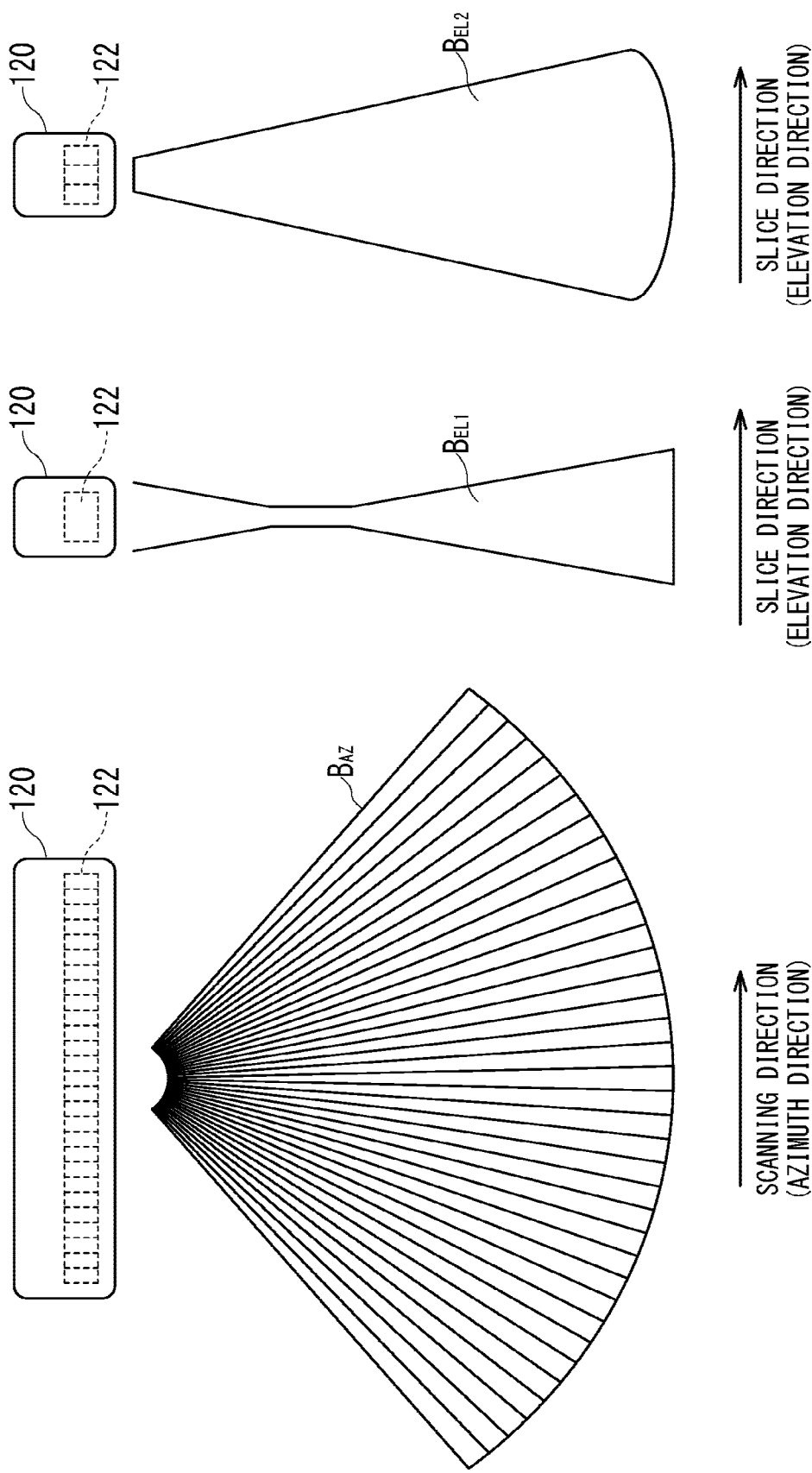
FIG. 3A is a schematic diagram illustrating a concept of a beam in an azimuth direction formed by a reception-side phase-matching adder.
FIG. 3B is a schematic diagram illustrating a beam shape in a slice direction of an ultrasonic probe which has a fixed focal point and forms a beam shape different from a fan shape.
FIG. 3C is a schematic diagram illustrating a beam shape in a slice direction of an ultrasonic probe which can form a fan beam.

FIG. 3A is a schematic diagram illustrating a concept of a beam $B_{AZ}$ in the azimuth direction formed by the receiving phase-compensation/summation circuit 234. Although each of the transducers inside the ultrasonic probe 120 has wide beam width in the azimuth direction, the beam $B_{AZ}$ with narrow beam width can be formed by summing up reception signals from the respective transducers as shown in FIG. 3A. The reception signal outputted from the receiving phase-compensation/summation circuit 234 of the receiving circuit 232 corresponds to narrow beam width in the azimuth direction, but keeps wide beam width in the elevation direction (i.e., the slice direction) determined by the size of the ultrasonic probe 120 in the lateral direction (i.e., shorter direction), as shown in FIG. 3B and FIG. 3C.

A beam shape in the slice direction may be a beam shape $B_{EL1}$ type, whose focal point is separated by a predetermined length from a non-illustrated lens of the ultrasonic probe 120, as shown in FIG. 3B. Alternatively, a beam shape in the slice direction may be a fan beam $B_{EL2}$ type as shown in FIG. 3C. The beam shape $B_{EL1}$ type shown in FIG. 3B corresponds to a 1D array probe. On the other hand, the fan beam $B_{EL2}$ in FIG. 3C can be achieved by a 2D array probe, 1.25D array probe, 1.5D array probe, or 1.75D array probe.

The 1D array probe has a fixed aperture in the lateral direction and has a fixed focal point. On the other hand, the 2D array probe is such a probe that arrangement of its transducers in the elevation direction is similar to arrangement of its transducers in the azimuth direction, and thus can perform an electronic scan and electronic focusing in both directions. As intermediate probes between the 1D array probe and the 2D array probe, a 1.25D array probe, a 1.5D array probe, and a 1.75D array probe are known. The 1.25D array probe has a fixed focal point and can change its aperture in the lateral direction. The 1.5D array probe can change its focal length and its aperture in the lateral direction, but its ultrasonic field in the lateral direction is symmetric about the center axis. The 1.75D array probe can change its focal length and its aperture in the lateral direction, and does not have the symmetric restriction on the ultrasonic field about the center axis. Thus, the 1.75D array probe is capable of beam scanning in the elevation direction, but has an upper limit of beam scanning in the elevation direction.

Returning to FIG. 2, the first processing circuitry 210 includes, e.g., a processor, and implements various types of functions by causing the processor to execute predetermined programs stored in the memory circuitry 241. The first processing circuitry 210 implements, e.g., a B-mode processing function 211, a color-mode processing function 212, a Doppler-mode processing function 213, a scan control function 214, an image analysis function 215, and a three-dimensional image processing function 216.

The B-mode processing function 211 generates a B-mode image by performing predetermined processing such as envelope detection and logarithmic conversion on a reception signal. The color-mode processing function 212 generates a color-mode image by performing predetermined processing such as moving target indicator (MTI) filter processing and/or autocorrelation processing on a reception signal. The Doppler-mode processing function 213 generates a spectrum image by performing predetermined processing such as Fourier transform on a reception signal. A color-mode image, a B-mode image, and a spectrum image generated in the above-manner are stored in the memory circuitry 241 configured of storage components such as a Hard Disk Drive (HDD).

Incidentally, the B-mode processing function 211, the color-mode processing function 212, and the Doppler-mode processing function 213 are collectively referred to as an image data generation function. This is because various types of image data such as a B-mode image, a color-mode image, and a spectrum image are generated by those functions.

Note that the following processing, which will be described below, such as aperture synthesis processing, transmission phase-compensation and summation processing, and/or spatial compound processing, is performed prior to the above-described processing performed by the B-mode processing function 211, the color-mode processing function 212, and the Doppler-mode processing function 213. In this case, a B-mode image, a color-mode image, or a spectrum image is generated based on data after the aperture synthesis processing, the transmission phase-compensation and summation processing, and/or the spatial compound processing. Images generated in the above manner and data related to those images are displayed on the display 250.

The scan control function 214 controls transmission/reception directions of an ultrasonic signal and a moving direction of the ultrasonic probe 120 so as to perform an ultrasonic scan on an object.

The image analysis function 215 performs various types of image analysis on ultrasonic images such as a B-mode image, a color-mode image, and a spectrum image, and causes the display 250 to display the analysis result. The three-dimensional image processing function 216 three-dimensionally reconstructs B-mode beam data and/or color-mode beam data acquired together with positional information so as to generate a cross-sectional image in a desired direction under a multi-planar reconstruction/reformation (MPR) method, and/or generate a three-dimensional image under a volume rendering (VR) method or a maximum intensity projection (MIP) method. The display 250 is a display device equipped with, e.g., a liquid crystal panel.

The input device 260 is a device for inputting various types of data and information by an operator's operation. The input device 260 may include, e.g., operation devices such as a keyboard, a mouse, a trackball, a joystick, and a touch panel and various types of information input devices such as a voice input device.

The memory circuitry 241 includes a semiconductor memory such as a read only memory (ROM), a random access memory (RAM), and an external memory device such as a hard disc drive (HDD) and/or an optical disc device.

The second processing circuitry 300 includes, e.g., a processor similarly to the first processing circuitry 210, and implements various types of functions by causing the processor to execute predetermined programs stored in the memory circuitry 241.

In addition to the above-described first processing circuitry 210 and the second processing circuitry 300, the arm control circuit 140 also includes a processor and implements various types of functions by causing the processor to execute predetermined programs stored in the arm control circuit 140 or in the memory circuitry 241.

The above-described term "processor" includes, e.g., a central processing unit (CPU) and a special-purpose or general-purpose processor. Additionally, various types of functions of the processor can be implemented by hardware processing, instead of software processing performed by the processor. For instance, each of the first processing circuitry 210, the second processing circuitry 300, and the arm control circuit 140 can be configured of hardware such as an application specific integrated circuit (ASIC), a programmable logic device (e.g., a simple programmable logic device (SPLD) and a complex programmable logic device (CPLD)), and a field programmable gate array (FPGA). Further, software processing by a processor and hardware processing may be combined for implementing various types of functions.

The second processing circuitry 300 implements, e.g., a probe position acquisition function 310, a signal acquisition function 311, an aperture synthesis processing function 312, and a spatial compound processing function 313.

(Operation)

Figure 4:
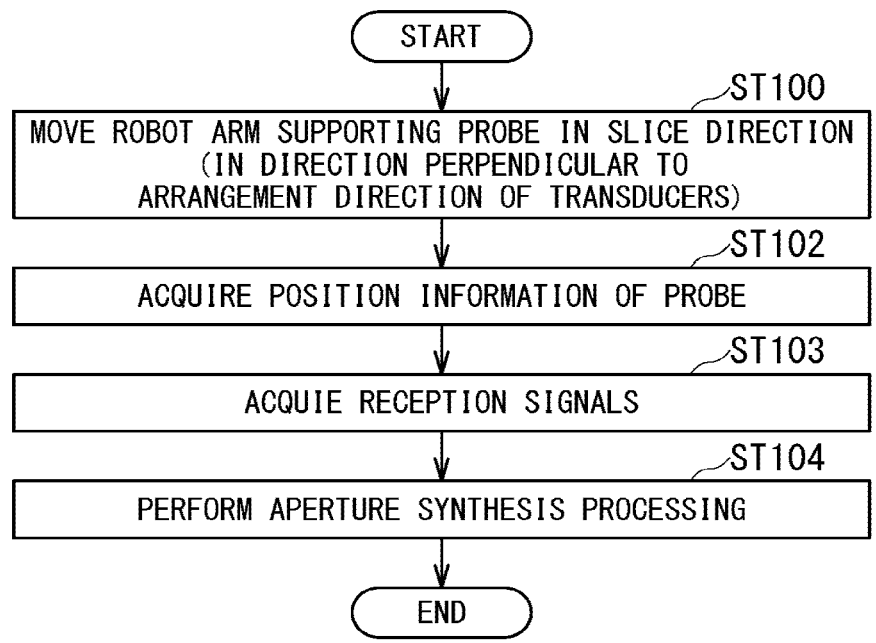
FIG. 4 is a flowchart illustrating aperture synthesis processing.

FIG. 4 is a flowchart illustrating an operation performed by the ultrasonic diagnostic apparatus 1 of the present embodiment. Hereinafter, the above-described functions implemented by the second processing circuitry 300 and the functions implemented by the arm control circuit 140 will be described in detail according to the step numbers in the flowchart of FIG. 4.

The step ST100 corresponds to processing implemented by the arm control circuit 140. In the step ST100, the arm control circuit 140 causes the robot arm 110 supporting the ultrasonic probe 120 to move in the direction perpendicular to the arrangement direction of the array of the transducers.

Figure 5:
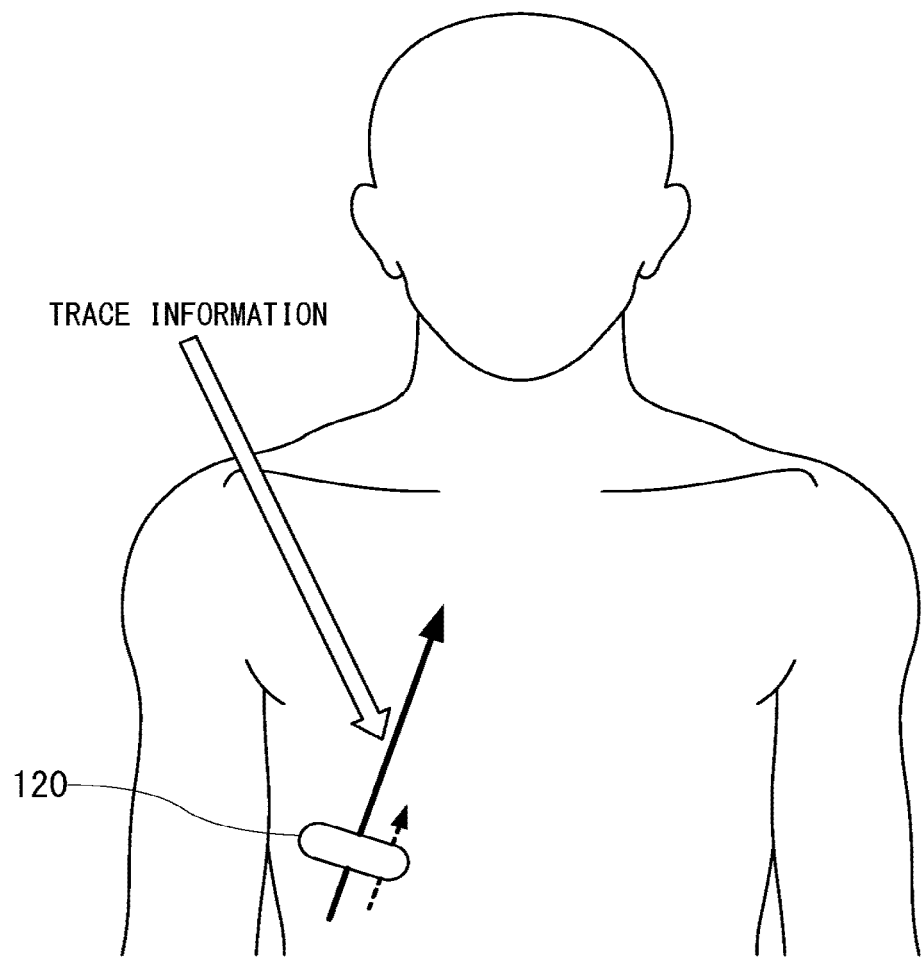
FIG. 5 is a schematic diagram illustrating movement of an ultrasonic probe controlled by a robot arm.

FIG. 5 is a schematic diagram illustrating movement of the ultrasonic probe 120 controlled by the robot arm 110. As shown in FIG. 5, the robot arm 110 moves the ultrasonic probe 120 in the direction perpendicular to the longitudinal direction (i.e., a longer direction) of the ultrasonic probe 120 according to trace information. In other words, the robot arm 110 moves the ultrasonic probe 120 in the direction perpendicular to the arrangement direction of the transducers. Note that the trace information is stored in the memory circuitry 241 in advance.

The step ST102 is processing corresponding to the probe position acquisition function 310. In the step ST102, the probe position acquisition function 310 sequentially acquires positional information of the ultrasonic probe 120 supported by the robot arm 110 from output signals of the arm sensor 111 mounted on the robot arm 110 and/or output signals of the probe sensor 112 mounted on the ultrasonic probe 120 during movement of the ultrasonic probe 120. The positional information to be acquired is three-dimensional positional information, and includes not only the position of the ultrasonic probe 120 in its moving direction but also the orientation of the ultrasonic probe 120 at each timing.

The step ST103 is processing corresponding to the signal acquisition function 311. In the step ST103, the signal acquisition function 311 acquires reception signals outputted from the receiving circuit 232 in real time during movement of the ultrasonic probe 120. The reception signals to be acquired in the step ST103 may be reception signals before beam formation of the respective transducers of the ultrasonic probe 120, or reception signals after a beam is formed in the azimuth direction. In the case of the reception signals after the beam is formed in the azimuth direction, the resolution is high in the azimuth direction, whereas the resolution in the slice direction (i.e., the elevation direction) is low. This is because size of the ultrasonic probe 120 in lateral direction is restricted.

The processing of the step ST102 and the processing of the step ST103 are simultaneously performed in parallel during movement of the ultrasonic probe 120 controlled by the robot arm 110. Each of the acquired reception signals is associated with the positional information of the ultrasonic probe 120 at its acquisition timing. Thus, the acquired reception signals are temporarily stored in, e.g., a RAM of the memory circuitry 241, together with the positional information of the ultrasonic probe 120.

Figure 6:
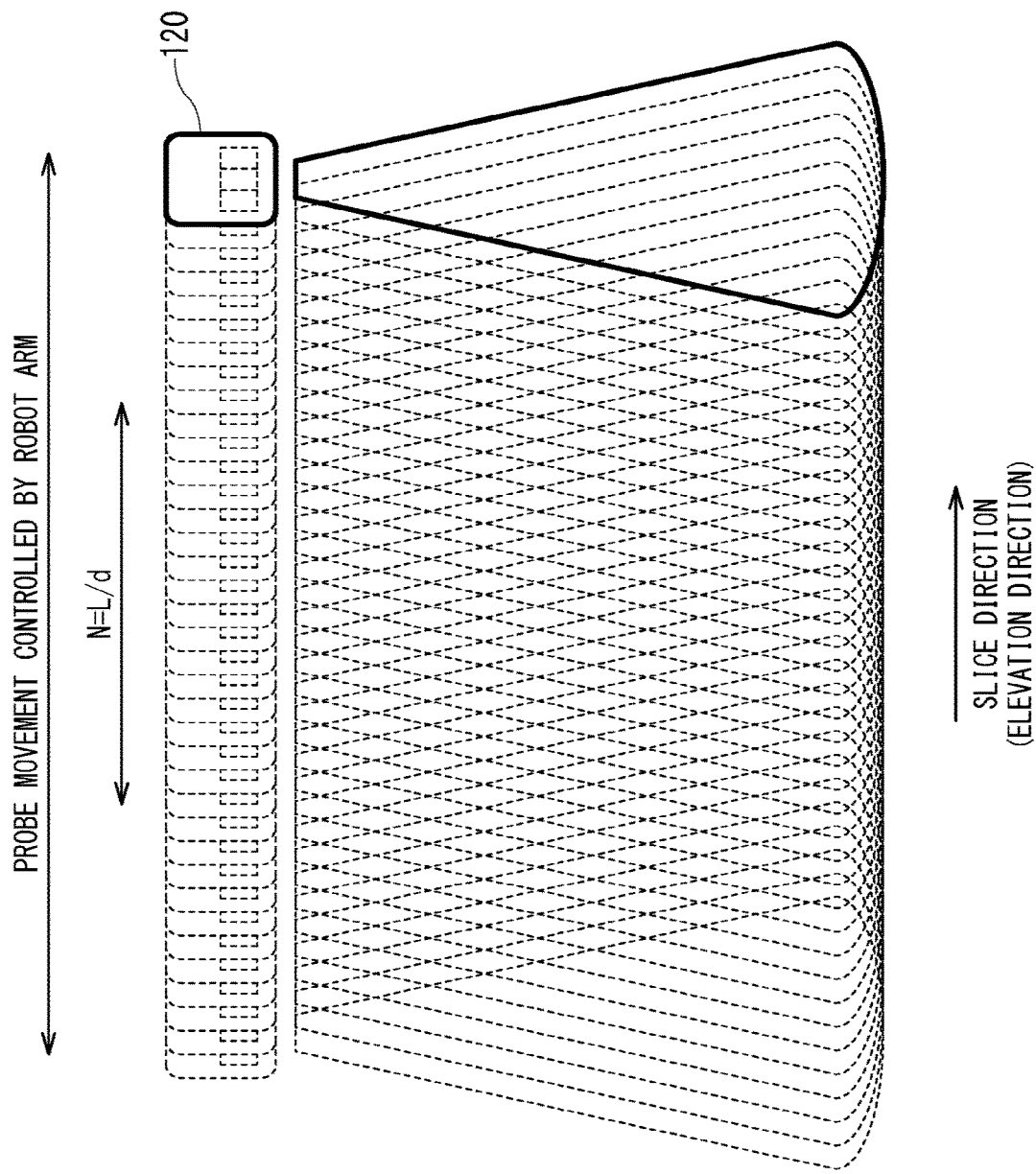
FIG. 6 is a schematic diagram illustrating movement of the ultrasonic probe controlled by the robot arm together with a beam shape (fan beam) of the ultrasonic probe in the slice direction.

FIG. 6 is a schematic diagram illustrating movement of the ultrasonic probe 120 controlled by the robot arm 110 together with a beam shape (fan beam) of the ultrasonic probe 120 in the slice direction (i.e., the elevation direction). Although reception signals are composed of signals corresponding to respective sampling positions in the depth direction of an object (i.e., in the range direction), the reception signals are acquired for the respective moving positions of the ultrasonic probe 120 and sequentially stored in the memory circuitry 241.

The step ST104 is processing corresponding to the aperture synthesis processing function 312. In the step ST104, the aperture synthesis processing function 312 reads out reception signals of a predetermined number N for the aperture synthesis processing and positional information of the ultrasonic probe 120 corresponding to those reception signals from the memory circuitry 241.

Figure 7:
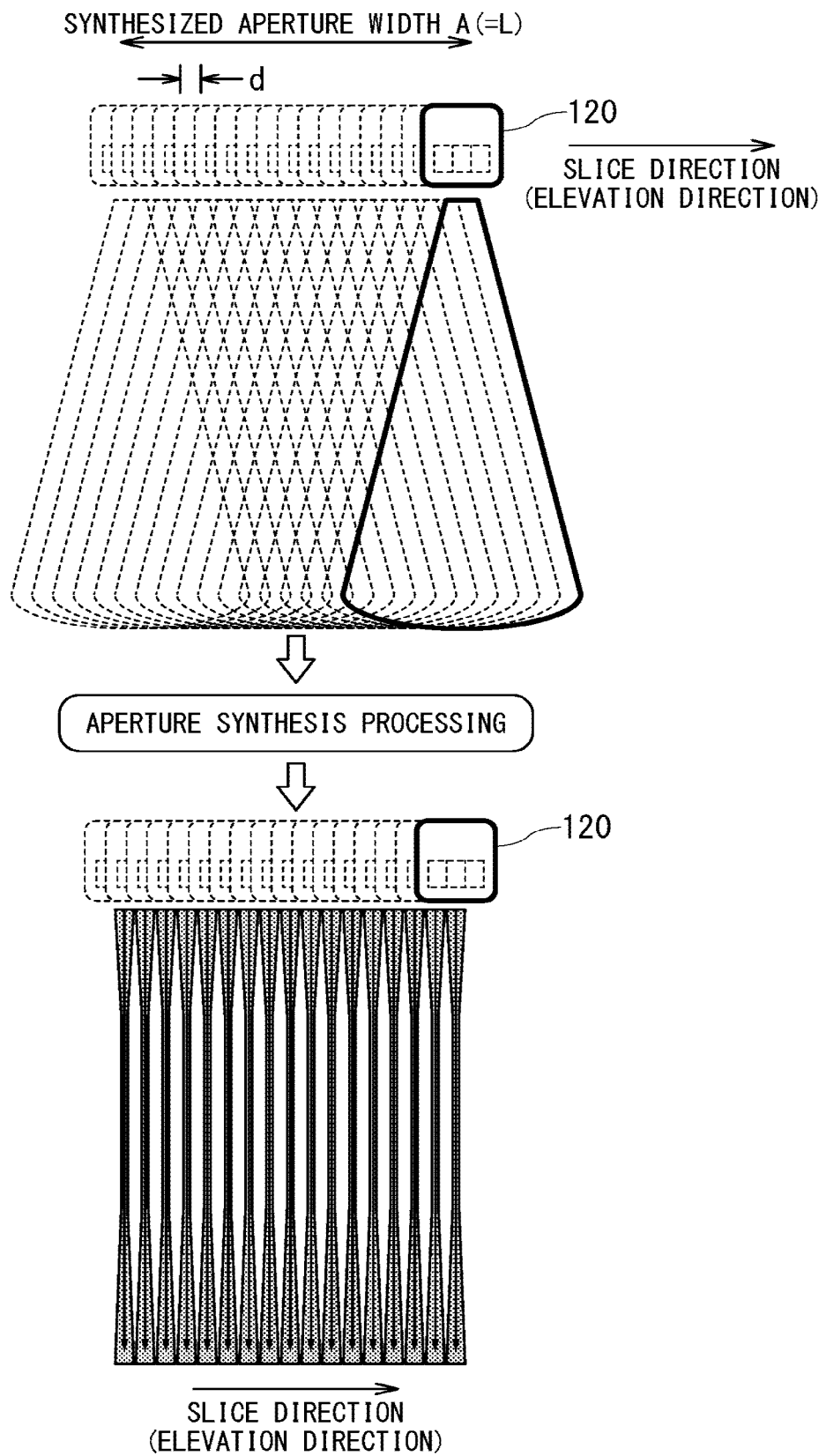
FIG. 7 is a schematic diagram illustrating a concept of the aperture synthesis processing.

FIG. 7 is a schematic diagram illustrating a concept of the aperture synthesis processing. The aperture synthesis processing function 312 provides a predetermined delay time to each of the reception signals acquired at an interval d, and then coherently sums up (i.e., adds or synthesizes) the respective reception signals. This processing is the aperture synthesis processing. Coherent summation is to sum up the respective reception signals under a condition where phase information of each of the reception signals is maintained, i.e., to sum up the respective reception signals as complex signals (or IQ signals). According to the aperture synthesis processing, a beam having narrow beam width in the slice direction (i.e., the elevation direction) can be formed and resolution in the slice direction (i.e., the elevation direction) can be enhanced.

Next, the aperture synthesis processing of the present embodiment will be described in detail in a case where a two-dimensional array probe (hereinafter, referred to as a 2DA probe) is used for the ultrasonic probe 120.

Figure 8:
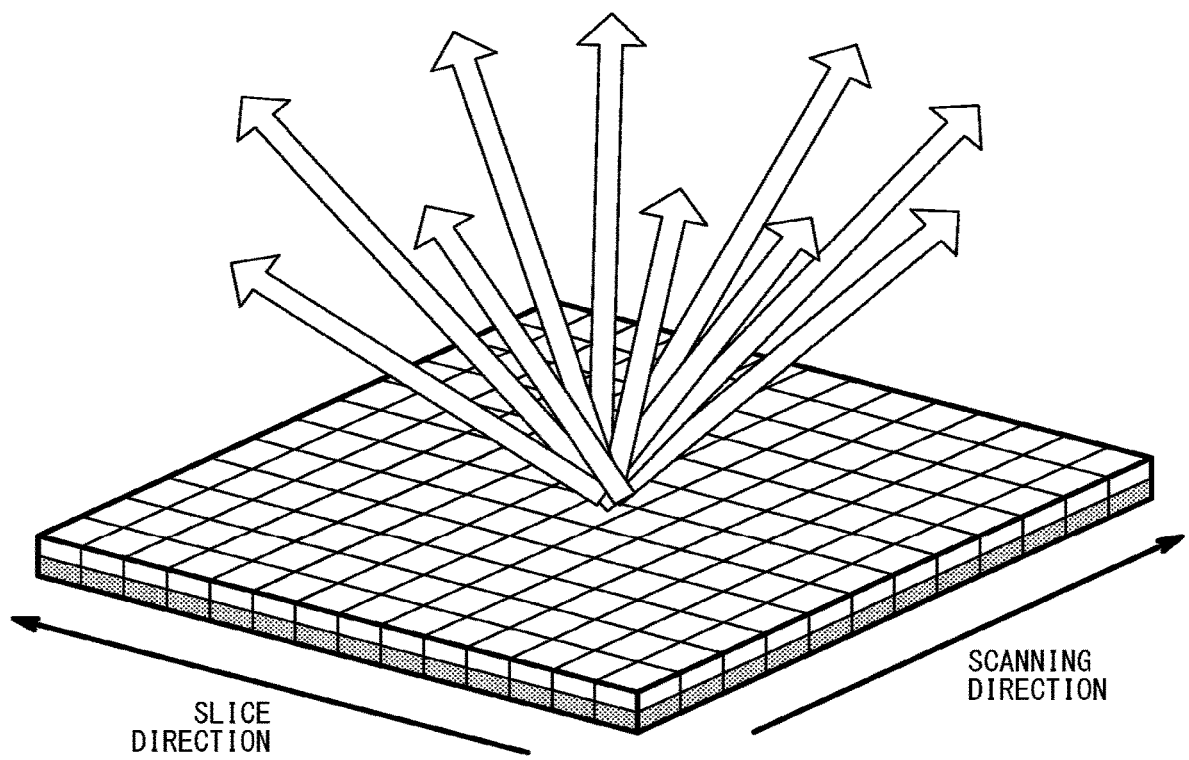
FIG. 8 is a schematic perspective view illustrating arrangement of transducers of a 2DA probe.

FIG. 8 is a schematic perspective view illustrating arrangement of transducers of a 2DA probe. The transducers are two-dimensionally arranged not only in the scanning direction but also in the slice direction. The respective transducers are electrically connected to the main body 200.

FIG. 9A is a schematic plan view illustrating arrangement of transducers of a 2DA probe, and FIG. 9B is a schematic perspective view illustrating scanning of a 2DA probe. Cross-sectional images in real time can be generated with the 2DA similarly to the usual one-dimensional array probe (hereinafter, referred to as a 1DA probe). Although a 2DA probe can generate a cross-sectional image in any direction, the direction along which more transducers are arranged, i.e., the cross-sectional direction in which higher image quality is obtained is defined as the scanning direction as shown in FIG. 9A. Meanwhile, the direction perpendicular to the scanning direction is defined as the slice direction.

The slice direction corresponds to a direction in which an ultrasonic beam is formed by an acoustic lens in the case of a 1DA probe. A 2DA probe often has anisotropy in arrangement of transducers, as shown in FIG. 9A, due to restrictions in terms of number of transducers and probe shape.

As shown in FIG. 9B, a real-time cross-sectional image is generated, basically, in the scanning direction. Meanwhile, transducers in the slice direction also contribute to beam formation in the slice direction. In the case of a 2DA probe, a cross-sectional image can be moved in the slice direction by electronically controlling beam formation in the slice direction. In the case of acquiring volume data with the use of a 2DA probe, the cross-section formed in the scanning direction is moved in the slice direction Each cross-sectional image in the slice direction can be moved not only electronically but also mechanically.

Figure 10:
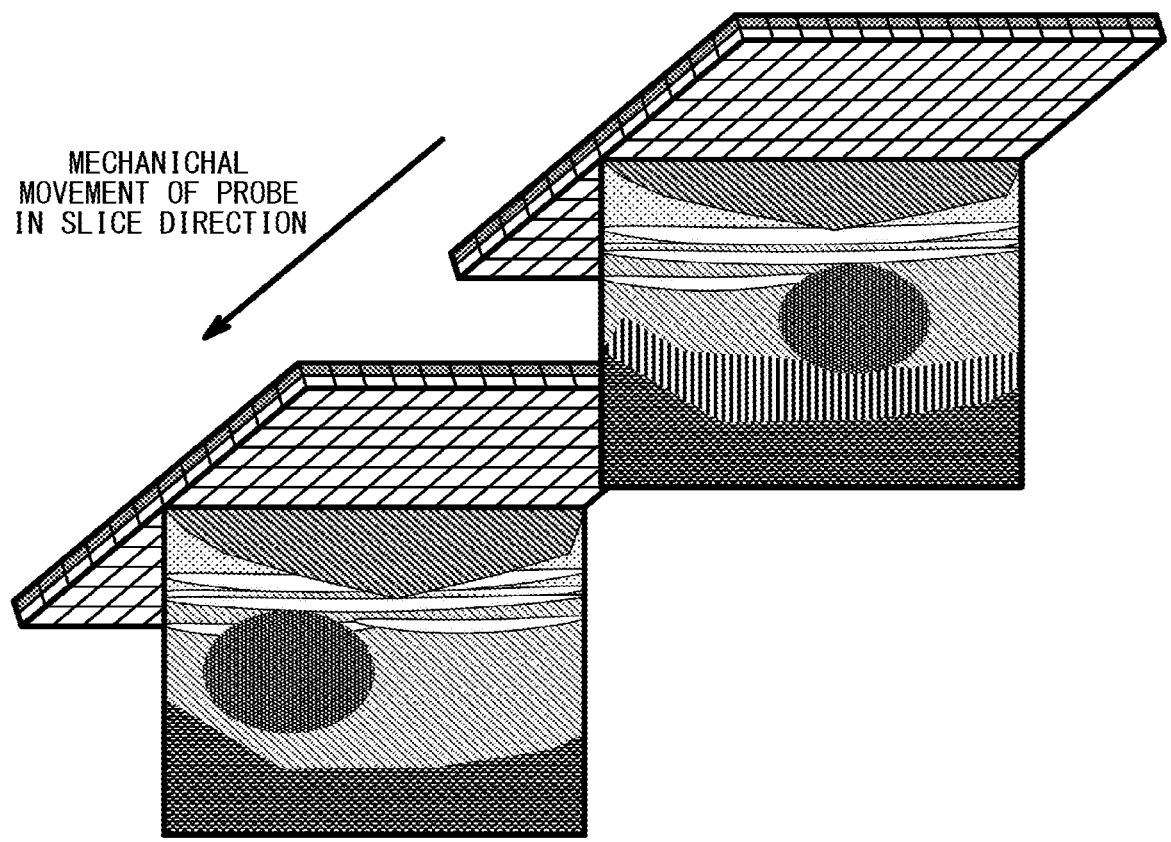
FIG. 10 is a schematic perspective view illustrating a method of mechanically moving a 2DA probe in the slice direction.

FIG. 10 is a schematic perspective view illustrating a method of mechanically moving a 2DA probe by using the robot arm 110 of the present embodiment. By scanning an object in the scanning direction with the use of a 2DA probe, the region directly under the 2DA probe is imaged as a cross-sectional image. Then, the region to be imaged as a cross-sectional image is moved in the slice direction by mechanically moving the 2DA probe so as to acquire volume data of each region directly under the moving 2DA probe. In this manner, volume data are successively acquired while the 2DA probe is mechanically moved.

FIG. 11A to FIG. 11D are schematic diagrams illustrating mechanical movement of a 2DA probe in the slice direction. Relationship between an ultrasonic beam and an observation point in three-dimensional space will be described focusing on a scanning plan formed directly under the aperture center of the 2DA probe.

FIG. 11A is a schematic perspective view illustrating relationship between a transducer plane of the 2DA probe and a scanning plane directly under the 2DA probe. A virtual plane in parallel with the transducer plane of the 2DA probe is set at a certain depth from a body surface, and observation points through which an ultrasonic beam passes are set on this virtual plane. Five observation points P1, P2, P3, P4, and P5 on the intersection line between this virtual plane and the scanning plane directly under the transducer plane of the 2DA probe are defined for respective five ultrasonic beams such that the five ultrasonic beams pass through the respective observation points P1 to P5.

FIG. 11B is a schematic diagram illustrating the condition of FIG. 11A when viewed along the slice direction (i.e., when viewed in the direction perpendicular to the moving direction of the 2DA probe). In the state of FIG. 11B, the scanning plane intersects the observation point P1. Note that the aperture width of the 2DA probe in the slice direction is defined as D.

FIG. 11C illustrates the condition of the 2DA probe mechanically moved by a distance Δd from the position of FIG. 11B when viewed along the slice direction. In FIG. 11C, the scanning plane directly under the 2DA probe is moved to a position intersecting the observation point Q1.

FIG. 11D illustrates the condition of the 2DA probe further mechanically moved by the distance Δd from the position of FIG. 11C to the position where the scanning plane intersects the observation point R1, when viewed along the slice direction.

In FIG. 11A, the respective five observation points on the intersection line between the virtual plane and the scanning plane including the observation point Q1 are illustrated as Q1 to Q5. Similarly, in FIG. 11A, the respective five observation points on the intersection line between the virtual plane and the scanning plane including the observation point R1 are illustrated as R1 to R5. Note that observation points directly under the 2DA probe shift by mechanically moving the 2DA probe.

FIG. 12A to FIG. 12C are schematic diagrams illustrating the aperture synthesis processing performed by mechanically moving the 2DA probe with the use of the robot arm 110.

The positions of the 2DA probe shown in FIG. 12A, FIG. 12B, and FIG. 12C correspond to the positions of the 2DA probe shown in FIG. 11B, FIG. 11C, and FIG. 11D, respectively. That is, in FIG. 12A to FIG. 12C, the scanning plane directly under the 2DA probe moves from the observation point P1 to Q1 and then from the observation point Q1 to R1 in a manner similar to the case of FIG. 11B to FIG. 11D.

When the aperture synthesis processing is performed, a beam passing through an observation point common to respective positions of the 2DA probe in FIG. 12A to FIG. 12C is formed, as shown by the arrow in each of FIG. 12A to FIG. 12C. For instance, at the position of the 2DA probe in FIG. 12A, a beam passing through the observation point P1 is formed and ultrasonic data are acquired using this beam. Then, also at the position of the 2DA probe in FIG. 12B, a beam passing through the observation point P1 is formed and ultrasonic data are acquired by electronically scanning the object in the slice direction with the use of the 2DA probe. Similarly, also at the position of the 2DA probe in FIG. 12C, a beam passing through the observation point P1 is formed and ultrasonic data are acquired by electronically scanning the object in the slice direction with the use of the 2DA probe.

Figures 13A, 13B, 13C, 13D:
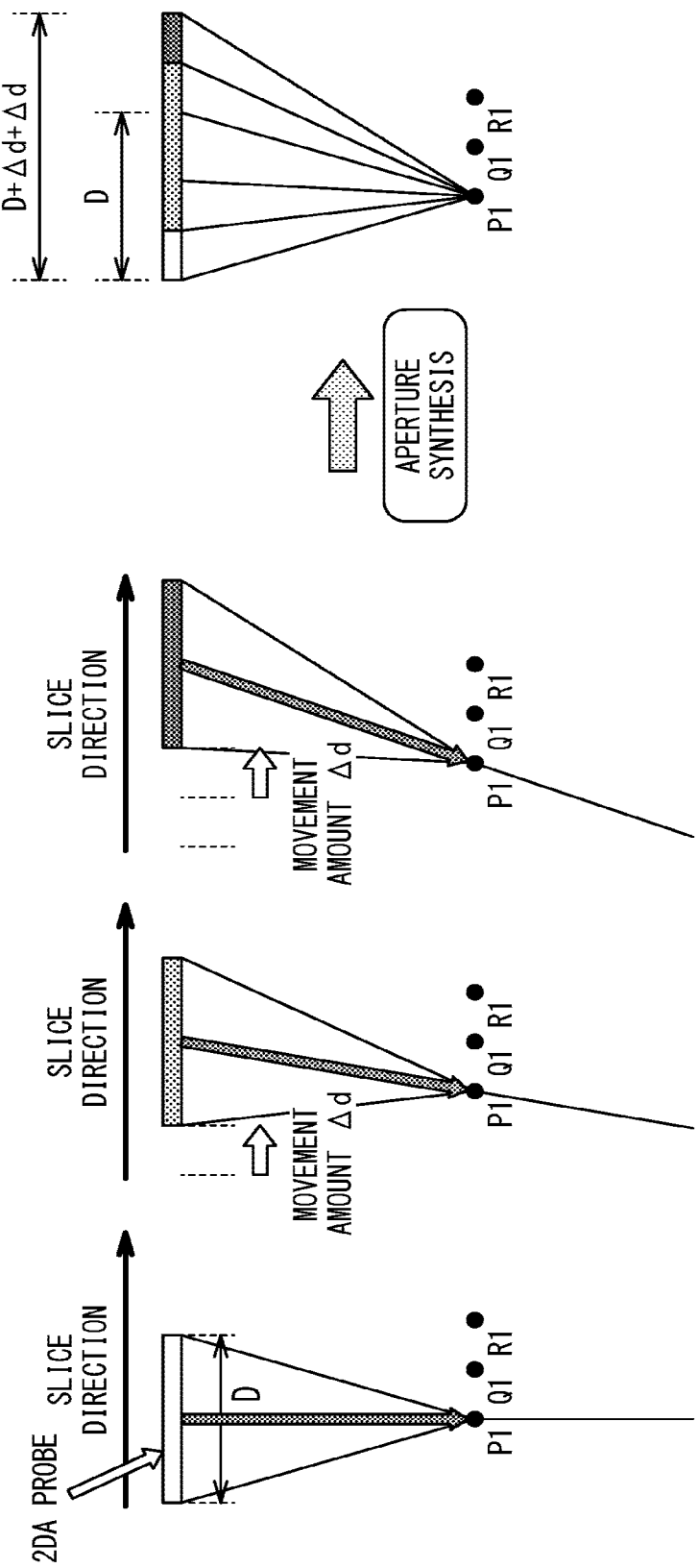
FIG. 13A to FIG. 13D are schematic diagrams illustrating the concept of mechanical movement of a 2DA probe and beam formation from a viewpoint different from FIG. 12A to FIG. 12C.

FIG. 13A to FIG. 13D are schematic diagrams illustrating the aperture synthesis processing performed by mechanically moving the 2DA probe with the use of the robot arm 110 from a viewpoint different from FIG. 12A to FIG. 12C. FIG. 13A to FIG. 13C respectively correspond to FIG. 12A to FIG. 12C, and show that echo signals from the observation point P1 are acquired at the respective probe positions of FIG. 13A to FIG. 13C.

After acquiring the echo signals from the observation point P1 at the respective probe positions of FIG. 13A to FIG. 13C, as shown in FIG. 13D, the aperture synthesis can be performed by using the echo signals from the observation point P1 acquired at the respective probe positions of FIG. 13A to FIG. 13C. In other words, the aperture synthesis is performed by setting predetermined delay amounts to the respective echo signals acquired at the respective probe positions of FIG. 13A to FIG. 13C and then coherently summing up those echo signals. According to this aperture synthesis, an effect that the aperture width in the slice direction is increased from D to D+2*Δd, and thus spatial resolution in the slice direction is enhanced.

The above-described aperture synthesis is performed by the aperture synthesis processing function 312 shown in FIG. 2.

Figure 14:
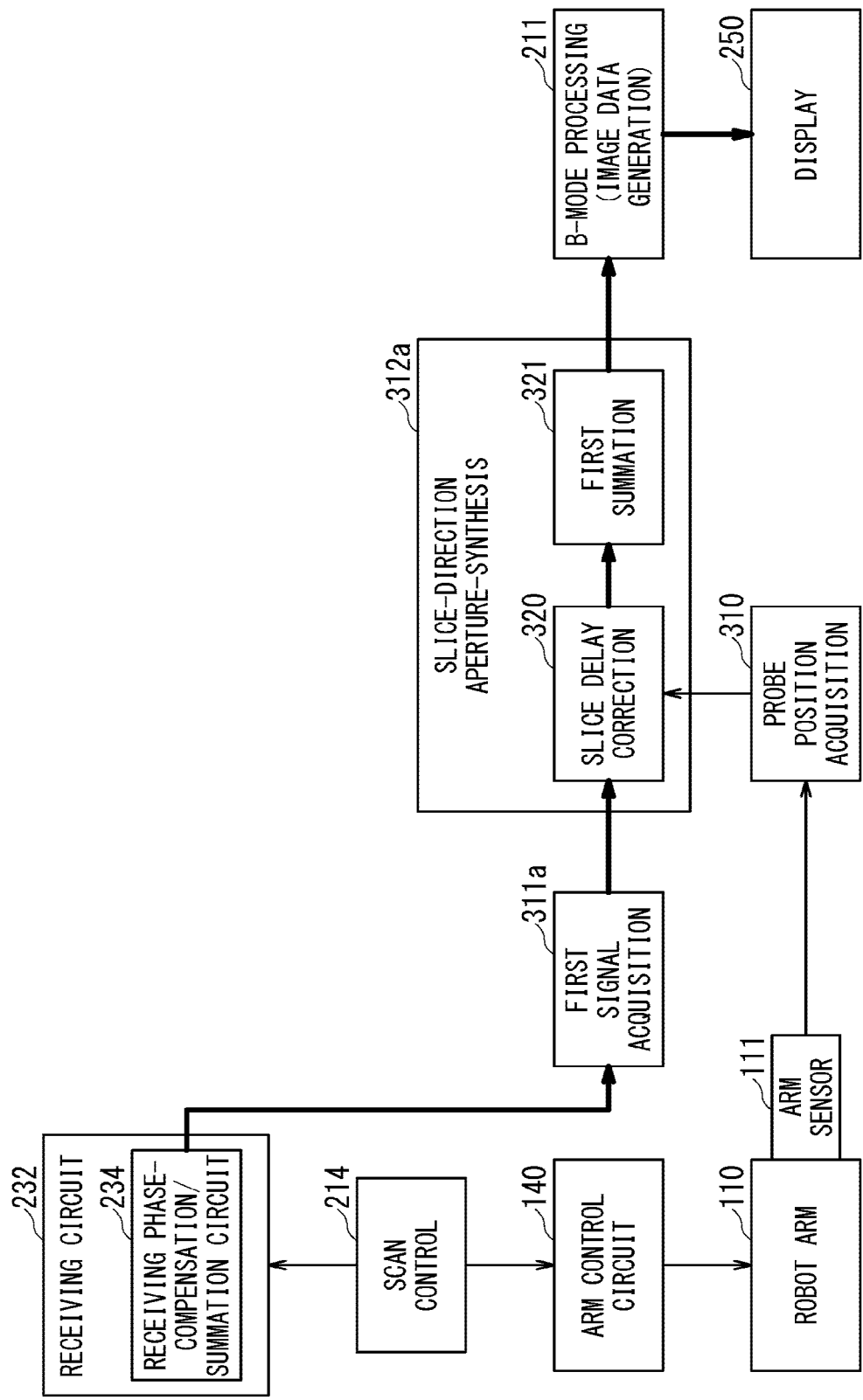
FIG. 14 is a detailed block diagram illustrating components related to the aperture synthesis processing achieved by mechanical movement of the ultrasonic probe in the slice direction.

FIG. 14 is a detailed functional block diagram illustrating components related to the aperture synthesis processing function 312. The positions of the 2DA probe shown in FIG. 13A, FIG. 13B, and FIG. 13C are respectively defined as a position A, a position B, and a position C. First, when the 2DA probe is at the position A, the receiving phase-compensation/summation circuit 234 of the receiving circuit 232 provides a desired delay amount to each of reception signals of the respective reception channels of the 2DA probe, and then sums up those reception signals. As the result, an echo signal corresponding to the observation point P1 under the condition where the 2DA probe is at the position A is obtained.

Next, the 2DA probe is mechanically moved by, e.g., the robot arm 110. When the moving means is a robot arm, positional information of the 2DA probe is acquired from the arm control circuit 140 or the arm sensor 111, and the probe position acquisition function 310 determines delay amounts such that the delay amounts correspond to the respective moving positions of the 2DA prove. The echo signals corresponding to the observation point P1 at respective moving positions of the 2DA probe are stored in the memory circuitry 241 by the first signal acquisition function 311a.

The slice delay correction function 320 of the slice-direction aperture-synthesis function 312a corrects the respective echo signals by adding each of the determined delay amounts to the corresponding echo signals for each moving position. Afterward, the first summation function 321 coherently sums up the respective echo signals so as to implement the aperture synthesis in the slice direction. The slice delay correction function 320 and the first summation function 321 constitute the slice-direction aperture-synthesis function (i.e., moving-aperture phase-compensation and summation function) 312a.

Although a robot arm is illustrated as a mechanical movement means, a mechanical movement means may be achieved by a mechanical 4D probe in which a structure for mechanically swinging the probe is included. Positional information of the probe can be acquired from, e.g., a drive circuit of a motor of the mechanical 4D probe.

FIG. 15A to FIG. 15D are schematic diagrams illustrating a concept of the aperture synthesis processing using a 1DA probe. A 1DA probe cannot scan a beam in the slice direction, and has fixed directivity in the directly downward direction due to its acoustic lens. In each of FIG. 15A to FIG. 15C, beam shape formed by the acoustic lens is schematically illustrated. The beam shape is determined by the focal point of the acoustic lens which is separated from the aperture center by the focal length in the slice direction.

Figure 15:
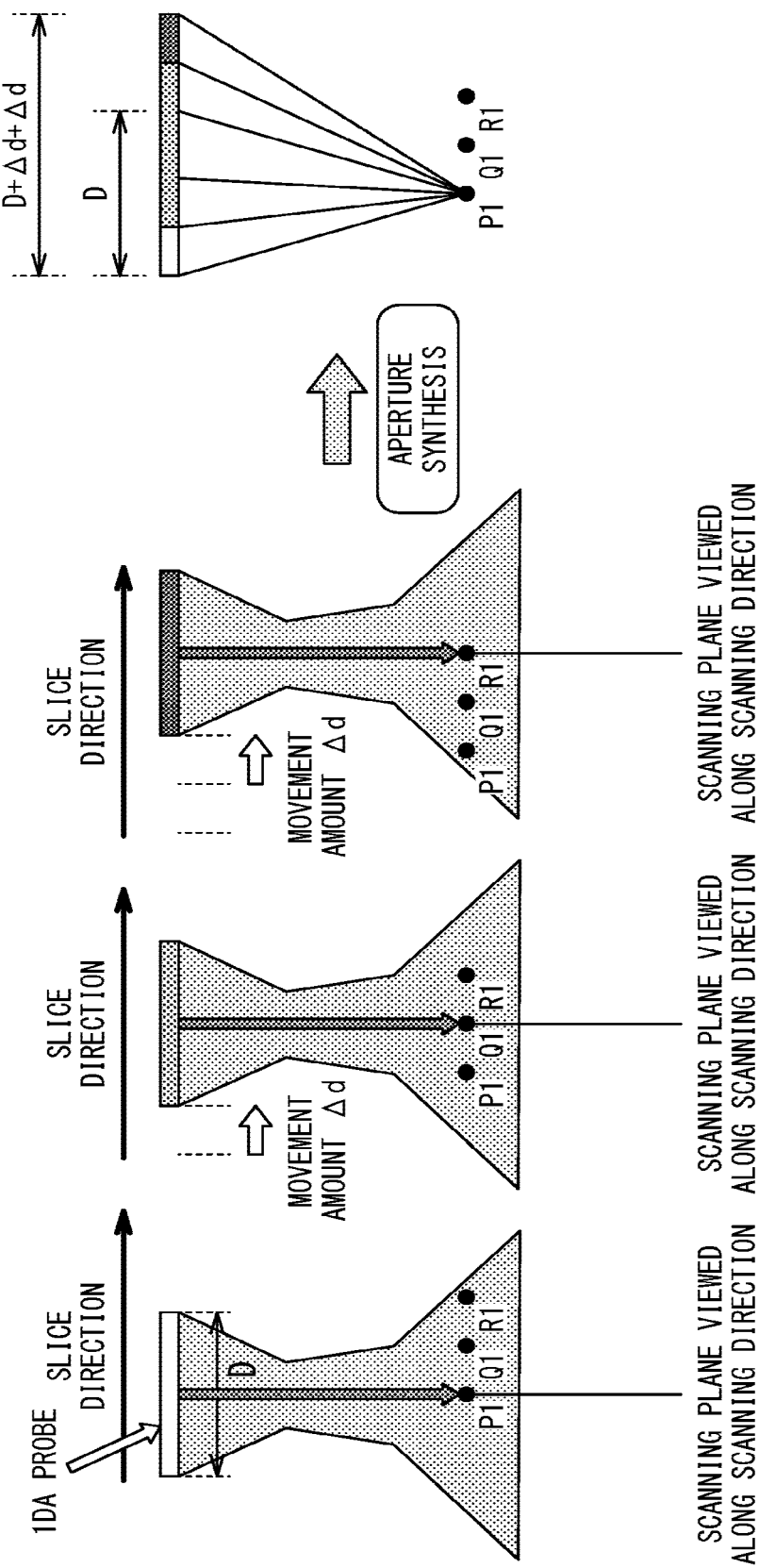
FIG. 15A to FIG. 15D are schematic diagrams illustrating a concept of the aperture synthesis processing using a 1DA probe.

As shown in FIG. 15A to FIG. 15C, the position of the beam passing through the observation point P1 changes by movement of the 1DA probe. Delay amounts with respect to the observation point P1 are set to the respective echo signals acquired in FIG. 15A, FIG. 15B, and FIG. 15C. Afterward, the delay amounts are added to the respective echo signals, and then those echo signals are coherently summed up such that the effect of the aperture synthesis can be obtained. The effect of increasing the aperture width in the slice direction from D to (D+2*Δd) is obtained.

The difference between the case of the 2DA probe in FIG. 13A to FIG. 13D and the case of the 1DA probe in FIG. 15A to FIG. 15D lies in beam width achieved before the aperture synthesis of the observation point P1. In the case of the 2DA probe, a narrow beam directed to the observation point P1 can be formed. Thus, the aperture synthesis is performed by shifting the aperture position while using the narrow beam. As for the 1DA probe, the aperture synthesis is performed with a broad width beam as schematically illustrated in FIG. 15A to FIG. 15C.

A flow of processing of the aperture synthesis using a 1DA probe and its functional block diagram are similar to the case of a 2DA probe described with FIG. 14 except that echo signals acquired by the first signal acquisition function 311a are different between both. In the case of a 2DA probe, an echo signal in which components of the respective observation points P1, Q1, and R1 are separated is acquired at each of movement positions of a 2DA probe. On the other hand, in the case of a 1DA probe, a synthesized and common echo signal in which components of the respective observation points P1, Q1, and R1 are not separated is acquired at each movement position. Correction of delay amounts corresponding to respective observation points P1, Q1, and R1 is performed on this common echo signal by the slice delay correction function 320 so that aperture synthesis is implemented.

Since the aperture synthesis shown in each of FIG. 13A to FIG. 13D and FIG. 15A to FIG. 15D is performed by moving a probe, it is sometimes referred to as moving aperture synthesis.

Figure 16:
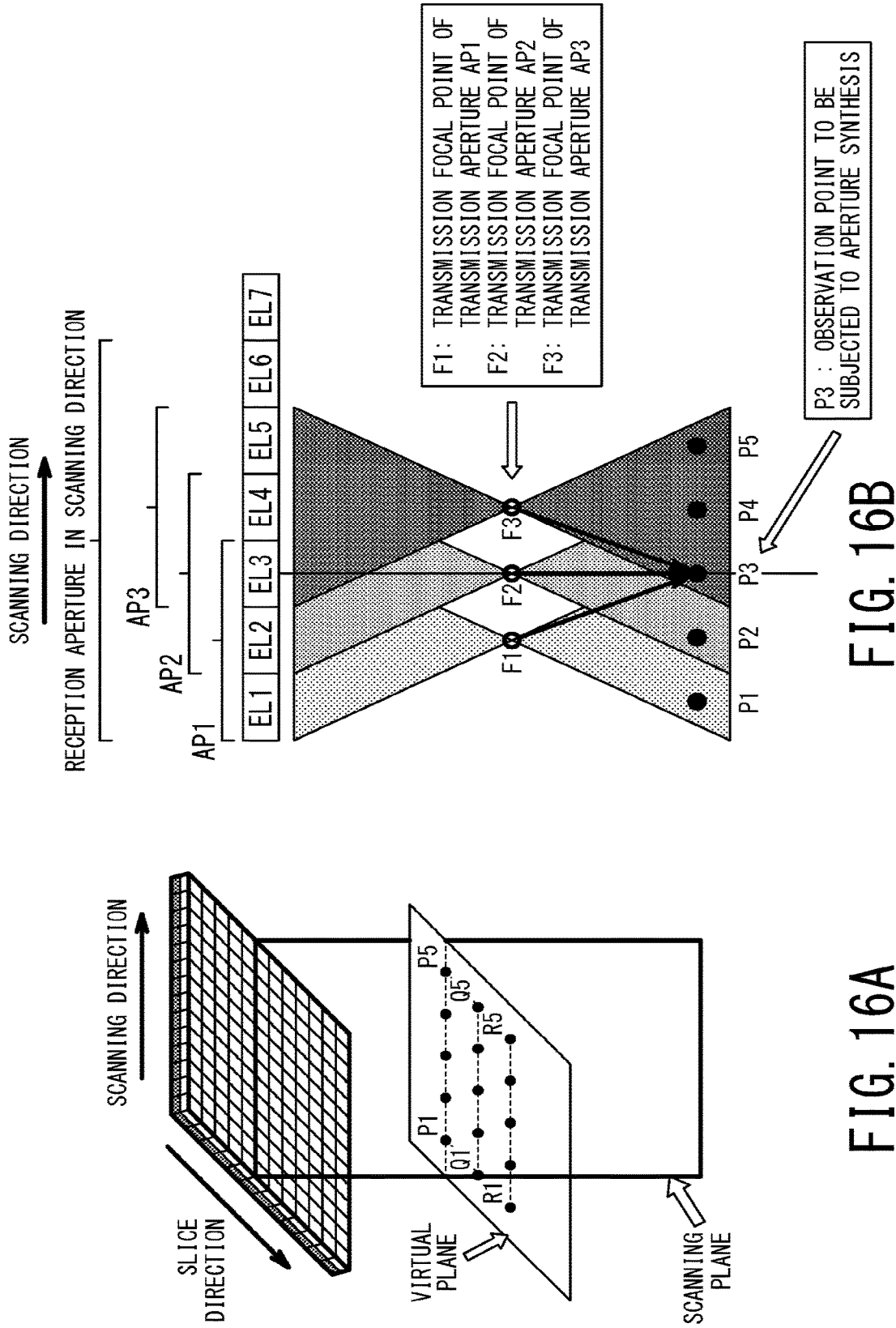
FIG. 16A and FIG. 16B are schematic diagrams illustrating a concept of an operation of transmission aperture-synthesis processing achieved by performing transmission phase-compensation and summation in the scanning direction as a modification of the aperture synthesis of a 2DA probe.

FIG. 16A and FIG. 16B are schematic diagrams illustrating a concept of an operation of transmission aperture-synthesis achieved by performing transmission phase-compensation and summation processing in the scanning direction as a modification of the aperture synthesis of a 2DA probe. Note the difference in direction between the above-described moving aperture synthesis and the transmission aperture-synthesis described below. The moving aperture synthesis is aperture synthesis processing performed in the slice direction while the 2DA probe is caused to move in the slice direction. On the other hand, the transmission aperture-synthesis is aperture synthesis processing performed in the scanning direction (i.e., in the direction perpendicular to the moving direction of the 2DA probe) while the 2DA probe is also caused to move in the slice direction. FIG. 16A is the same as FIG. 11A. The upper part of FIG. 16B schematically illustrates arrangement of transducers of a 2DA probe in the scanning direction. In FIG. 16B, only seven transducers EL1 to EL7 are illustrated for simplicity.

As an instance here, three types including a transmission aperture AP1 to a transmission aperture AP3 are assumed as partial transmission apertures. The transmission aperture AP1 corresponds to the first transmission transducer set composed of three transducers EL1, EL2, and EL3. The transmission aperture AP2 corresponds to the second transmission transducer set composed of three transducers EL2, EL3, and EL4. Similarly, the transmission aperture AP3 corresponds to the third transmission transducer set composed of three transducers EL3, EL4, and EL5. Further, it is assumed that the reception aperture corresponds to the reception transducer set composed of the six transducers EL1 to EL6.

As to the transmission aperture AP1, an ultrasonic beam is transmitted toward a virtual point sound source formed by the three transducers EL1 to EL3, i.e., toward the transmission focal point F1. That is, in transmission from the transmission aperture AP1, respective transmission delay amounts of the transducers EL1, EL2, and EL3 constituting the transmission aperture AP1 are set in such a manner that the transmission focal point F1 is formed at a predetermined focal position. Here, it is assumed that the observation point is P3. The ultrasonic beam transmitted from the transmission aperture AP1 passes through the transmission focal point F1 and then passes through the observation point P3 while widening its beam width. The ultrasonic signal reflected on or scattered at the observation point P3 is received by the six transducers EL1 to EL6. An echo signal from the observation point P3 corresponding to transmission from the transmission aperture AP1 is generated by performing the receiving phase-compensation and summation processing on the respective ultrasonic signals received by the six transducers EL1 to EL6.

The receiving phase-compensation and summation processing means to sum up respective reception signals for generating an echo signal at a certain observation point after correcting the respective reception signals such that relative delay times attributable to difference in propagation distance from this observation point to each of reception elements become substantially equal to each other. In the above-described case, the receiving phase-compensation and summation processing is to coherently sum up the respective reception signals of the transducers EL1 to EL6 after correcting the delay times of the respective reception signals such that the relative delay times attributable to difference in propagation distance from the observation point P3 to each of the transducers EL1 to EL6 become equal to each other.

Similarly, an ultrasonic beam is transmitted from the transmission aperture AP2 toward a virtual point sound source formed by the three transducers EL2 to EL4, i.e., toward the transmission focal point F2. This ultrasonic beam passes through the transmission focal point F2 and then the observation point P3 while widening its beam width. Afterward, an ultrasonic signal reflected on or scattered at the observation point P3 is received by the six transducers EL1 to EL6. An echo signal from the observation point P3 corresponding to transmission from the transmission aperture AP2 is generated by performing the receiving phase-compensation and summation processing on the respective ultrasonic signals received by the six transducers EL1 to EL6 in a similar manner as described above.

Similarly, an ultrasonic beam is transmitted from the transmission aperture AP3 toward a virtual point sound source formed by the three transducers EL3 to EL5, i.e., toward the transmission focal point F3. This ultrasonic beam passes through the transmission focal point F3 and then the observation point P3 while widening its beam width. The ultrasonic signal reflected on or scattered at the observation point P3 is received by the six transducers EL1 to EL6. An echo signal from the observation point P3 corresponding to transmission from the transmission aperture AP3 is generated by performing the receiving phase-compensation and summation processing on the respective ultrasonic signals received by the six transducers EL1 to EL6 in a similar manner as described above.

Each transmission focal point (i.e., each point sound source) is updated from F1 to F2 and from F2 to F3 by sequentially switching the transmission apertures AP1 to AP3. Then, three echo signals from the observation point P3 corresponding to the respective transmission apertures AP1 to AP3 are acquired.

Although those three echo signals are subjected to the receiving phase-compensation and summation processing such that difference in path length on the reception side (i.e., difference in distance from the observation point P3 to each of the transducers EL1 to EL6) is canceled, path length on the transmission side is different between the transmission apertures AP1 to AP3. In other words, propagation distances from the observation point P3 to the respective transmission focal points F1 to F3 are different from each other.

Thus, delay times in accordance with distances between the observation point P3 and the respective updated point sound sources are calculated, then three echo signals from the observation point P3 corresponding to the respective transmissions from the transmission apertures AP1 to AP3 are corrected such that the calculated delay times become equal to each other. Then, those three echo signals are coherently summed up. This processing is referred to as transmission phase-compensation and summation processing, and is also referred to as transmission aperture synthesis, because an effect of aperture synthesis is obtained by the transmission phase-compensation and summation processing.

In other words, the transmission phase-compensation and summation processing or the transmission aperture synthesis is processing of (a) dividing one transmission aperture in, e.g., the scanning direction into plural partial transmission apertures overlapping each other, (b) acquiring plural reception signals corresponding to respective transmissions from the plural partial transmission apertures, (c) correcting respective delay times of the plural reception signals such that delay times from a predetermined observation point to respective positions of transmission focal points formed at the respective partial transmission apertures become substantially equal to each other, and (d) generating an echo signal of the predetermined observation point by summing up the plural corrected reception signals.

When the above-described transmission aperture synthesis is not performed, the transmission focal points are fixed to determined depth such as F1, F2, and F3 shown in FIG. 16B. As shown in FIG. 16B, width of a transmitted ultrasonic beam is broad at depths other than the focal points positions F1, F2, and F3. In contrast, by performing the above-described transmission aperture synthesis, the effect of narrowing width of the ultrasonic beam can be obtained at any observation point, such as P3 other than the focal points Note that the present embodiment, the transmission aperture synthesis is performed in the scanning direction. Thus, an ultrasonic beam can be kept narrow and uniform from a shallow region to a deep region of an object in the scanning direction by performing the transmission aperture synthesis in the scanning direction, resulting in that resolution in the scanning direction can be enhanced. Further, signal to noise ratio is improved because plural reception signals corresponding to respective transmission apertures are summed up by the transmission aperture synthesis, and thus sensitivity is improved.

Further, both of the transmission aperture synthesis in the scanning direction and the moving aperture synthesis in the slice direction shown in FIG. 13A to FIG. 13D and FIG. 15A to FIG. 15D are performed in the present embodiment. As a result, an ultrasonic beam can be further narrowed not only in the scanning direction but also in the slice direction, and thus an ultrasonic image with higher resolution in both of the scanning direction and the slice direction can be obtained.

Figure 17:
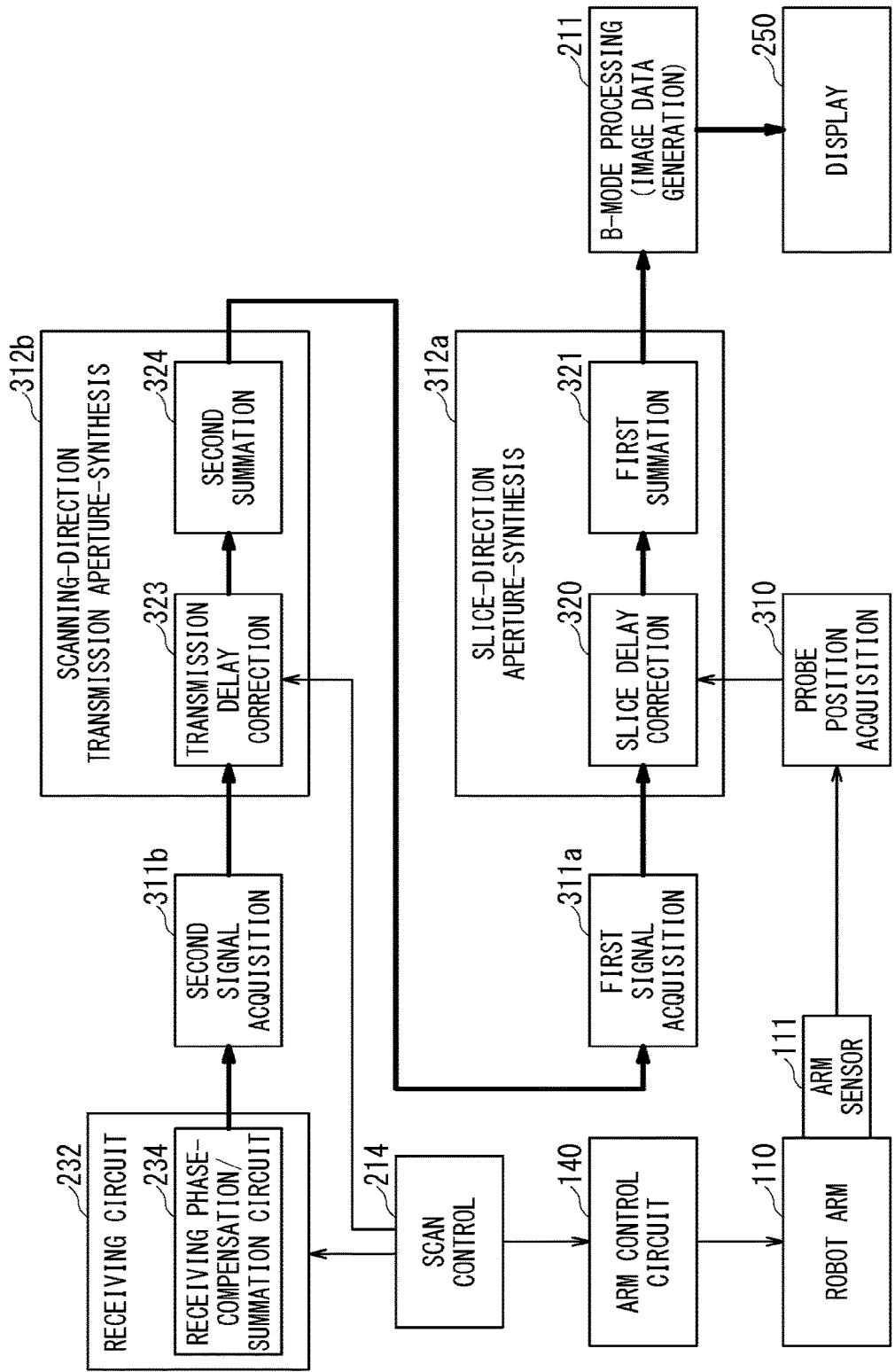
FIG. 17 is a block diagram of components for performing both of the transmission aperture synthesis in the scanning direction and the aperture synthesis in the slice direction.

FIG. 17 is a block diagram of components for performing both of the transmission aperture synthesis in the scanning direction and the moving aperture synthesis in the slice direction. Respective reception signals of reception channels of a 2DA probe are provided with predetermined delay amounts separately set for the respective reception channels, and then are subjected to the phase-matching addition (i.e., the receiving phase-compensation and summation processing) so as to be synthesized into an echo signal corresponding to the observation point, such as P3. First, an echo signal corresponding to the observation point P3 of the transmission aperture AP1 is stored in the memory circuitry 241 by the second signal acquisition function 311b.

Similarly, an echo signal corresponding to the observation point P3 of the transmission aperture AP2 and an echo signal corresponding to the observation point P3 of the transmission aperture AP3 are generated and stored in the memory circuitry 241 by the second signal acquisition function 311b. As to the three stored echo signals corresponding to the respective transmission apertures AP1, AP2, and AP3, each echo signal from the observation point P3 is subjected to the phase-matching addition (i.e., the transmission phase-compensation and summation processing). The transmission phase-compensation and summation processing is performed in such a manner that those three echo signals are provided with respective predetermined delay amounts by the transmission delay correction function 323 of the scanning-direction transmission aperture-synthesis function 312b and then are summed up by the second summation function 324. As a result, an echo signal of the observation point P3 subjected to the transmission aperture synthesis in the scanning direction is generated.

The slice-direction aperture-synthesis function 312a performs the aperture synthesis in the slice direction on the echo signals of the observation point P3 having been subjected to the transmission aperture synthesis in the scanning direction. The ultrasonic probe is moved by a mechanical method such as a robot arm. When the moving means is a robot arm, positional information of the ultrasonic probe is acquired from the arm control circuit 140 or the arm sensor 111, and delay amounts are determined for respective probe positions by the probe position acquisition function 310. Respective echo signals corresponding to the observation point P3 are stored for each probe position in the memory circuitry 241 by the first acquisition function 311a. Afterward, determined delay amounts are provided to the respective stored echo signals by the slice delay correction function 320, and then, echo signals of the respective moving positions are coherently summed up by the first summation function 321 so that the aperture synthesis in the slice direction is achieved.

There are at least two methods for the aperture synthesis in the slice direction. One of them is to perform the aperture synthesis at the observation point P3 by scanning a beam in the slice direction as shown in FIG. 13A to FIG. 13D, and another of them is to perform the aperture synthesis in the slice direction at the observation point P3 without scanning a beam in the slice direction as shown in FIG. 15A to FIG. 15D.

Various types of modifications are possible for the above-described embodiments. The transmission aperture synthesis in the scanning direction shown in FIG. 16A and FIG. 16B can be applied to a 2DA probe in the slice direction. In other words, the transmission aperture synthesis shown in FIG. 16A and FIG. 16B is performed in the slice direction before movement of an ultrasonic probe, and the moving aperture synthesis shown in FIG. 13A to FIG. 13D is further performed in the slice direction after the movement of the ultrasonic probe.

As a modification in the case of a 1DA probe or a 2DA probe, the aperture synthesis in the scanning direction shown in FIG. 16A and FIG. 16B may be performed without performing the aperture synthesis in the slice direction which involves probe movement as shown in FIG. 13A to FIG. 13D.

Additionally, in the case of a 1DA probe, the aperture synthesis in the scanning direction shown in FIG. 16A and FIG. 16B may be performed in combination with the aperture synthesis in the slice direction which involves probe movement as shown in FIG. 15A to FIG. 15D.

Further, both of the aperture synthesis in the scanning direction and the aperture synthesis in the slice direction may be performed such that transmission/reception conditions of ultrasonic waves are different between both. For instance, combination of transmission/reception conditions such as a transmission/reception frequency, aperture width, and a focal point may be changed between both.

In order to successfully achieve the above-described aperture synthesis processing, it is required to precisely move the ultrasonic probe 120 with accuracy sufficiently finer than wavelength of an ultrasonic wave inside an object's body. Such accuracy is hardly achieved when an operator holds the ultrasonic probe 120 with the hand to move it, and such accuracy can be achieved only when the ultrasonic probe 120 is supported by the robot arm 110 and mechanically moved.

So far, descriptions have been given for a case where the aperture synthesis is achieved by mechanically moving the ultrasonic probe 120. However, the ultrasonic diagnostic apparatus 1 of some embodiments can perform spatial compound processing by mechanically moving the ultrasonic probe 120. Hereinafter, the spatial compound processing of the present embodiment will be described. Since the spatial compound processing of the present embodiment is performed while the aperture of the ultrasonic probe 120 is caused to mechanically move, the spatial compound processing of the present embodiment is also referred to as moving aperture compound processing.

Figure 18:
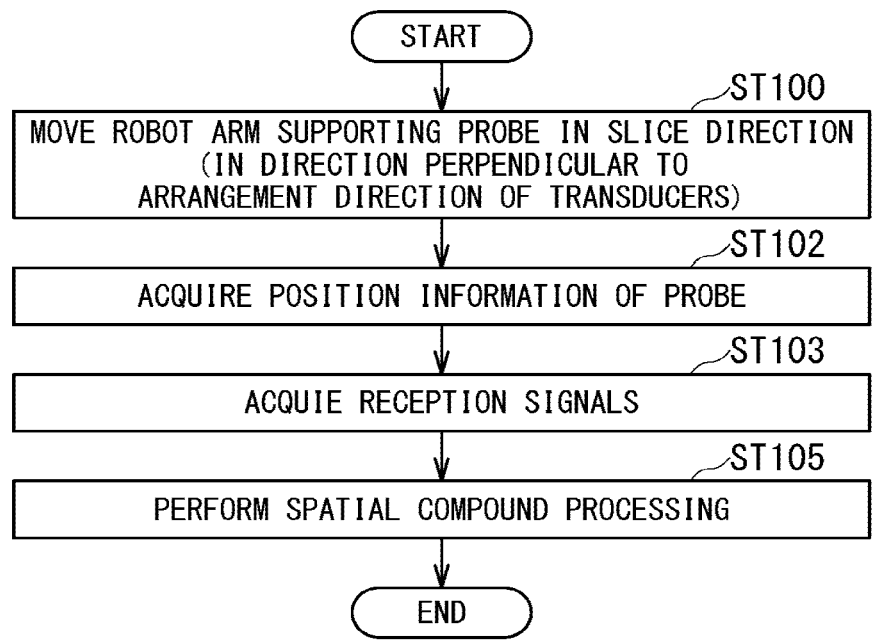
FIG. 18 is a flowchart illustrating spatial compound processing.

FIG. 18 is a flowchart illustrating the spatial compound processing of the present embodiment. Since the processing from the steps ST100 to ST103 is the same as the above-described aperture synthesis processing, duplicate description is omitted. In the step ST105, the spatial compound processing is performed.

The processing of the step ST105 corresponds to the spatial compound processing function 313 in FIG. 2. The spatial compound processing is processing of incoherently summing up (i.e., synthesizing) plural reception signals acquired by transmitting each ultrasonic wave and receiving each reception signal to/from the same position in plural different directions. The incoherent summation is processing of summing up (i.e., synthesizing) reception signals such that phase information of each of the reception signals is eliminated in the summation, and is, e.g., processing of converting respective reception signals acquired as complex signals into amplitude signals, and then summing up the respective reception signals, which is converted to the amplitude signals, into one synthesized signal. The spatial compound processing provides an effect that homogeneity of parenchyma is increased and spatial continuity of echo signals from an outer border of a lesion area is improved.

Conventional spatial compound processing using a 1DA probe, which is performed without mechanical movement of the probe, is performed in two-dimensional space, i.e., within an azimuth plane. By contrast, in the present embodiment, dimension number is increased and a spatial compound processing in three dimension space is achieved. Thus, the effect of spatial compound can be further enhanced.

Figure 19:
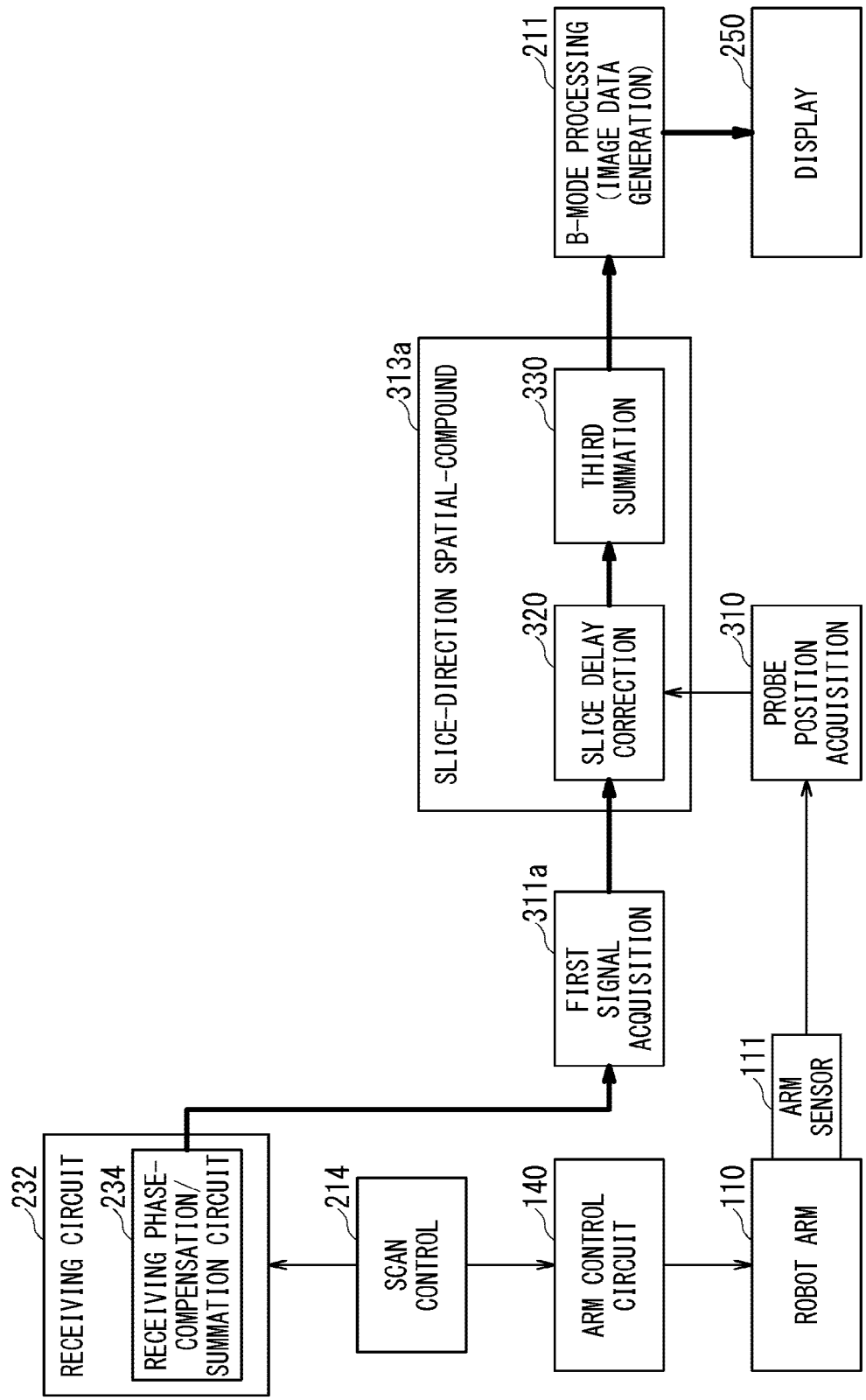
FIG. 19 is a functional block diagram of respective components relevant to the spatial compound function achieved by mechanical movement in the slice direction.

FIG. 19 is a functional block diagram of respective components relevant to the spatial compound function. The ultrasonic diagnostic apparatus 1 of this embodiment includes a slice-direction spatial-compound function 313a as a moving aperture compound function in order to perform the spatial compound processing. The moving aperture compound function includes a slice delay correction function 320 and a third summation function 313b.

In the spatial compound processing, similarly to the moving aperture synthesis, echo signals corresponding to the observation point P1 are also acquired for the respective moving positions of a 2DA probe by mechanically moving the 2DA probe. Afterward, the acquired echo signals are provided with respective delay amounts in accordance with probe positions of their acquisition timings. Thus, the receiving phase-compensation/summation circuit 234, the first acquisition function 311a, the probe position acquisition function 310, and the slice delay correction function 320 in FIG. 19 are substantially equal to the corresponding functions in FIG. 14. The difference between the spatial compound processing and the moving aperture synthesis lies in summation function.

In the moving aperture synthesis, the first summation function 321 in FIG. 14 performs the aperture synthesis by coherently summing up plural echo signals acquired for respective probe positions. Meanwhile, in the spatial compound processing, the third summation function 330 in FIG. 19 performs the spatial compound processing by incoherently summing up plural echo signals acquired for respective probe positions.

Figure 20:
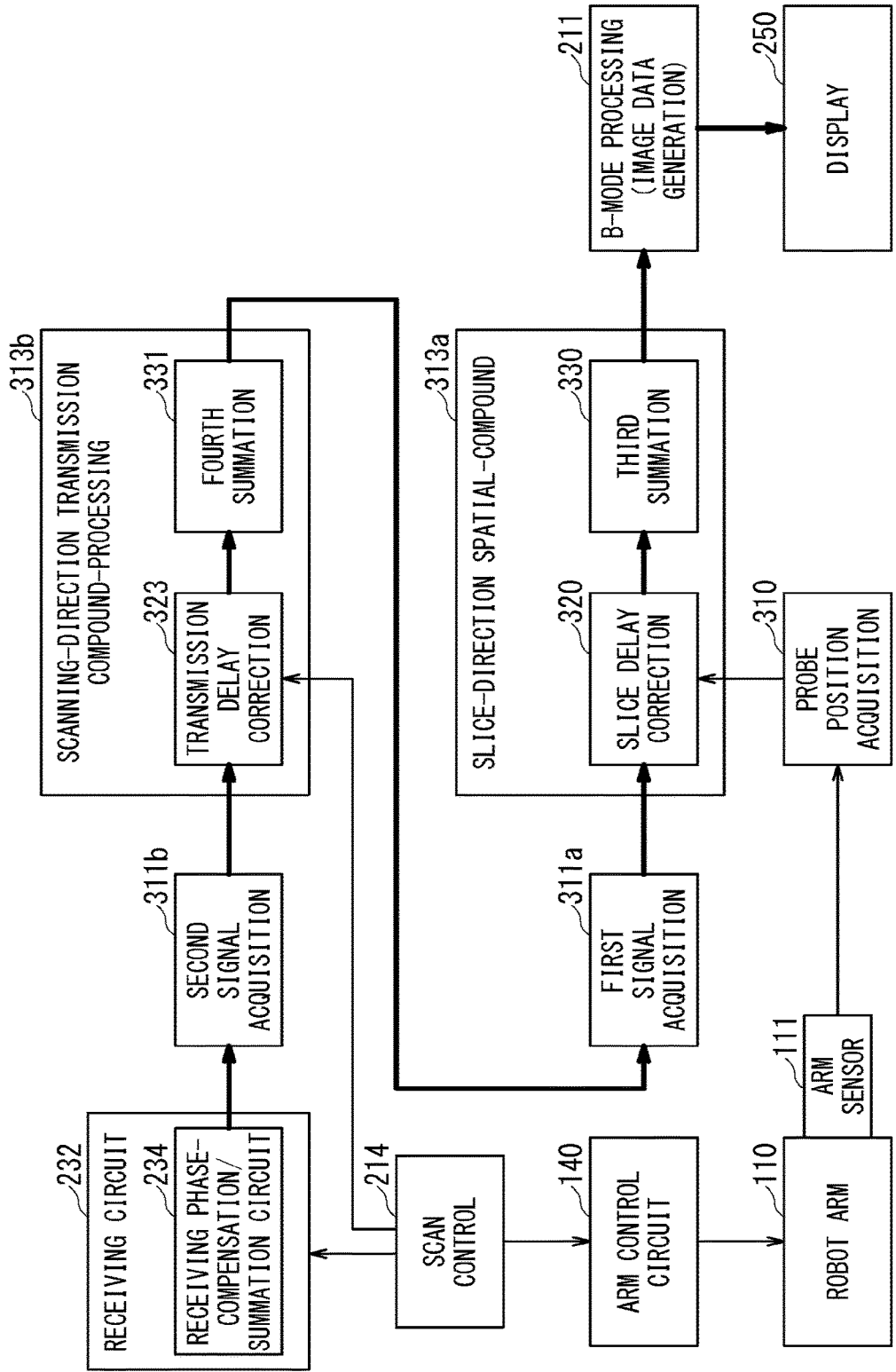
FIG. 20 is a functional block diagram in a case where the spatial compound processing is performed not only in the slice direction but also in the scanning direction.

FIG. 20 is a functional block diagram in a case where the spatial compound processing is performed not only in the slice direction but also in the scanning direction. The spatial compound processing function shown in FIG. 20 corresponds to the aperture synthesis processing shown in FIG. 17.

In the configuration of FIG. 20, a second signal acquisition function 311b and a scanning-direction transmission compound-processing function 313b are further included in addition to the components shown in FIG. 19. The scanning-direction transmission compound-processing function 313b includes a transmission delay correction function 323 and a fourth summation function 331.

The second signal acquisition function 311b and the transmission delay correction function 323 in FIG. 20 are the same as those in FIG. 17.

Although the second summation function 324 in FIG. 17 configured to perform the transmission aperture synthesis processing coherently sums up plural signals, the fourth summation function 331 in FIG. 20 configured to perform the spatial compound incoherently sums up plural signals. The incoherent summation implemented by the third summation function 330 and the incoherent summation implemented by the fourth summation function 331 enable spatial compound processing both in the slice direction and in the scanning direction.

As to the above-described embodiment of the spatial compound, various types of modifications are possible. For instance, the spatial compound processing and the aperture synthesis processing may be performed in combination. Additionally, the spatial compound processing in the scanning direction is not limited to processing performed by the scanning-direction transmission compound-processing function 313 shown in FIG. 20. For instance, the same observation point can be electronically scanned plural times in the scanning plane, and the echo signals acquired in this manner can be subjected to the spatial compound processing.

Additionally, transmission/reception conditions can be changed each time the spatial compound processing is performed. For instance, conditions such as a desired transmission/reception frequency, desired aperture width, and a desired focal point can be combined. Further, the compound processing is not limited to a spatial dimension. Different transmission frequencies may be used for the compound processing, additionally or alternatively to the different spatial directions.

Meanwhile, when the ultrasonic probe 120 is moved by the robot arm 110, it is required that the ultrasonic probe 120 is moved in contact with a body surface of an object. Thus, predetermined biological contact pressure can be included in the trace information for driving the robot arm 110. Then, by driving the robot arm 110 such that a detected value of the pressure sensor of the robot arm 110 matches this predetermined biological contact pressure, the ultrasonic probe 120 can be moved in contact with a body surface at the predetermined biological contact pressure.

Further, since a body surface of the object is not usually flat, the ultrasonic probe 120 fluctuates in a direction perpendicular to a body surface during its movement.

Figure 21:
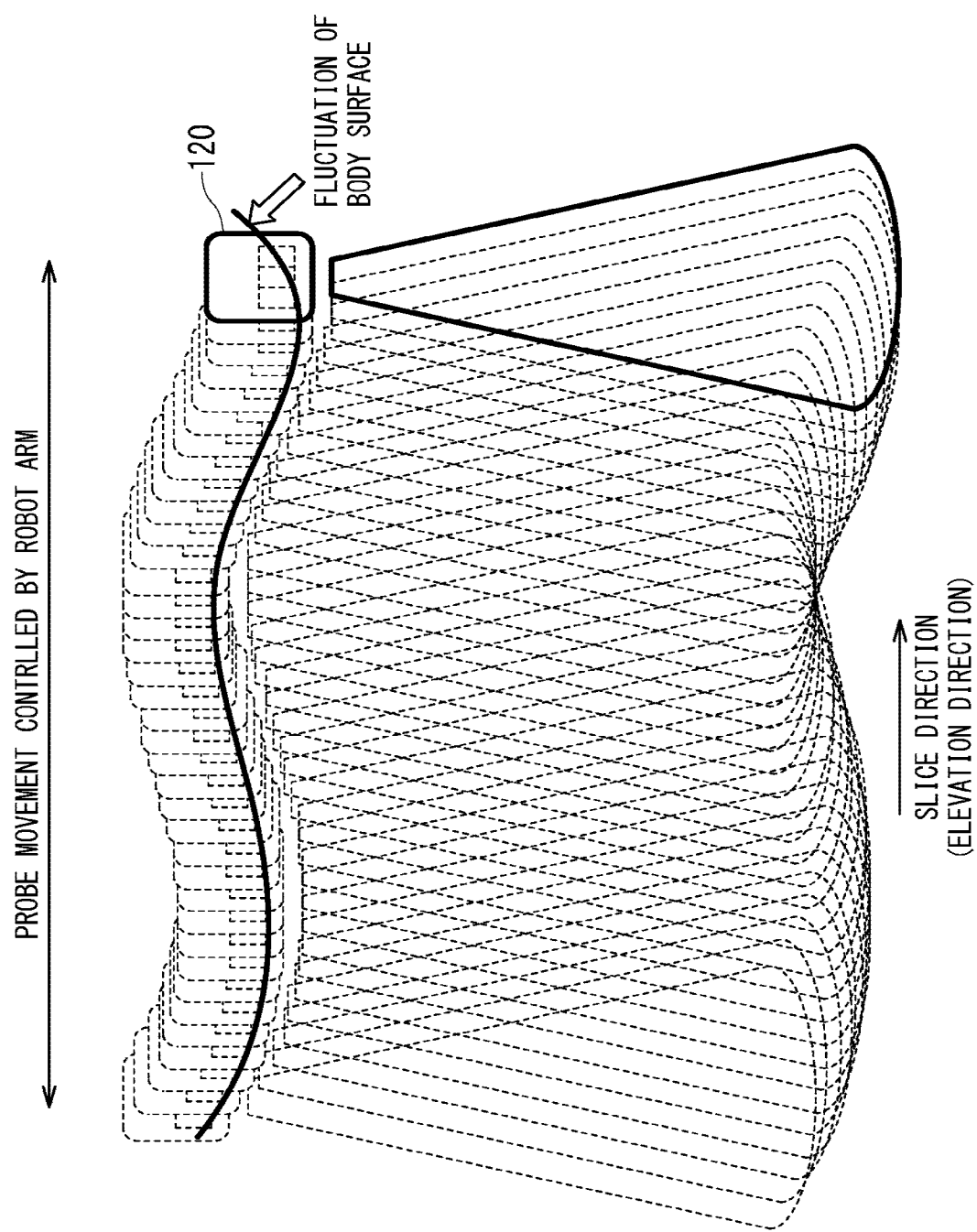
FIG. 21 is a schematic perspective view illustrating movement status of the ultrasonic probe controlled by the robot arm together with fluctuation of a body surface.

FIG. 21 is a schematic perspective view illustrating fluctuation in a direction perpendicular to a body surface. Additionally, even if the ultrasonic probe 120 is at the same position on a body surface of an object, the body surface fluctuates due to factors such as respiration, heartbeat, and change in posture, which changes the spatial position of the ultrasonic probe 120.

In the present embodiment, however, the arm sensor 111 is mounted on the robot arm 110 and three-dimensional positional information of the ultrasonic probe 120 is acquired by the arm sensor 111 as described above. In other words, fluctuation in the direction perpendicular to a body surface can be detected. Thus, the aperture synthesis processing function 312 can correct respective delay amounts before coherent summation by using the detected fluctuation amounts for respective probe positions so as to cancel the fluctuation of the body surface. Similarly, the compound processing function 313 can correct respective delay amounts before incoherent summation by using the detected fluctuation amounts for respective probe positions so as to cancel the fluctuation of the body surface.

As mentioned above, even if the ultrasonic probe 120 is configured such that its aperture width in the slice direction is smaller than its aperture width in the azimuth direction (i.e., scanning direction), and the resolution in the slice direction is lower than the resolution in the azimuth direction, a three-dimensional image with high resolution can be acquired. That is, even in such a case, a three-dimensional image with high resolution both in the azimuth and slice directions can be acquired by moving the ultrasonic probe 120 in the slice direction by the robot arm 110 and by performing the aperture synthesis processing on the reception signals acquired during this movement. Additionally, since the fluctuation of the ultrasonic probe 120 when moving on the body surface can be canceled by correction, a three-dimensional image of satisfactory image quality can be stably acquired over a wide scanning range.

Figure 22:
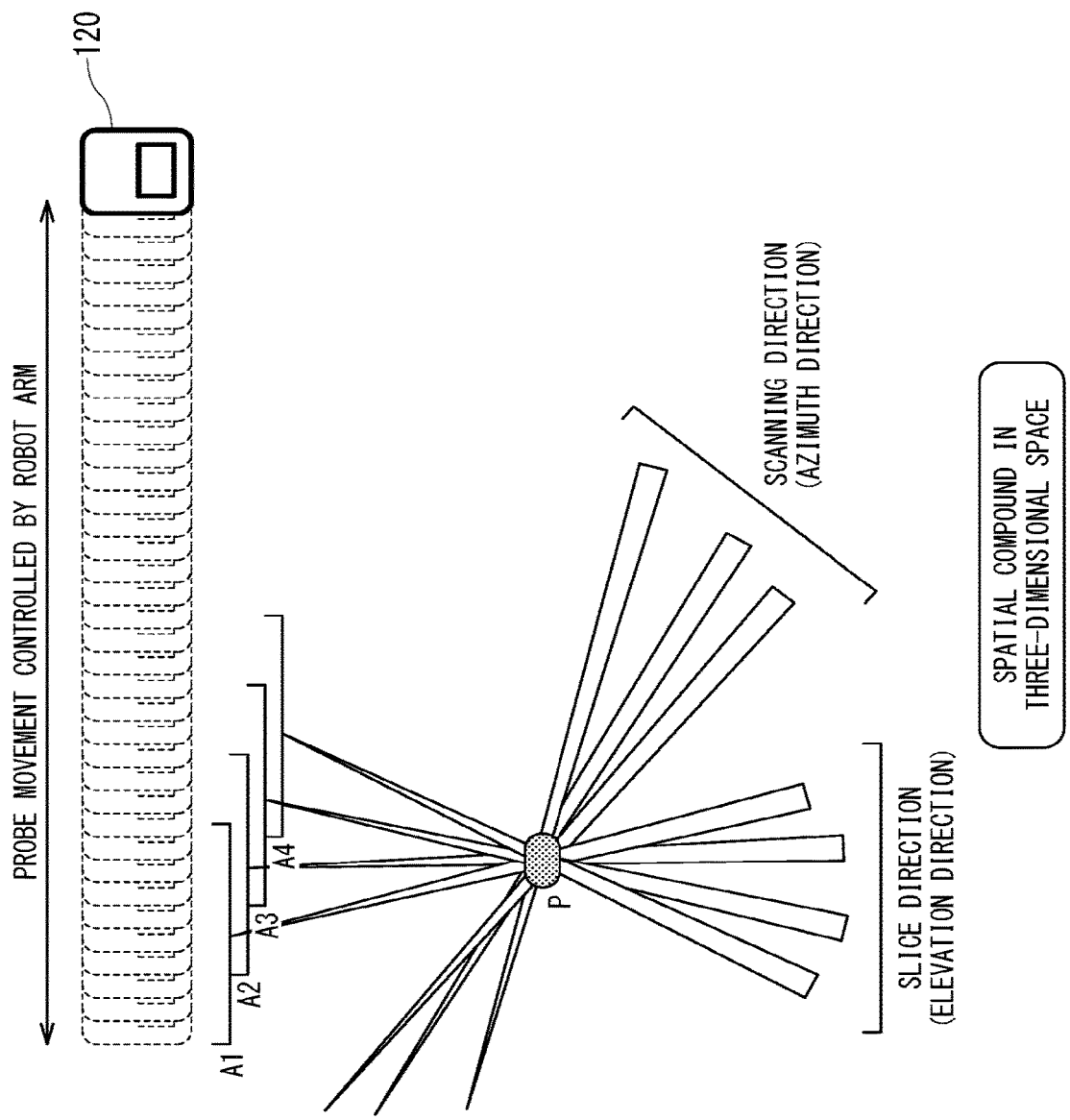
FIG. 22 is a schematic diagram illustrating a concept of three-dimensional spatial compound processing.

FIG. 22 is a schematic diagram illustrating a concept of the spatial compound processing in three-dimensional space. An ultrasonic probe can be moved in a desired direction by a robot arm, and plural reception signals from the same region can be subjected to the compound processing by scanning the same region plural times in different directions and using positional information.

Figure 9:
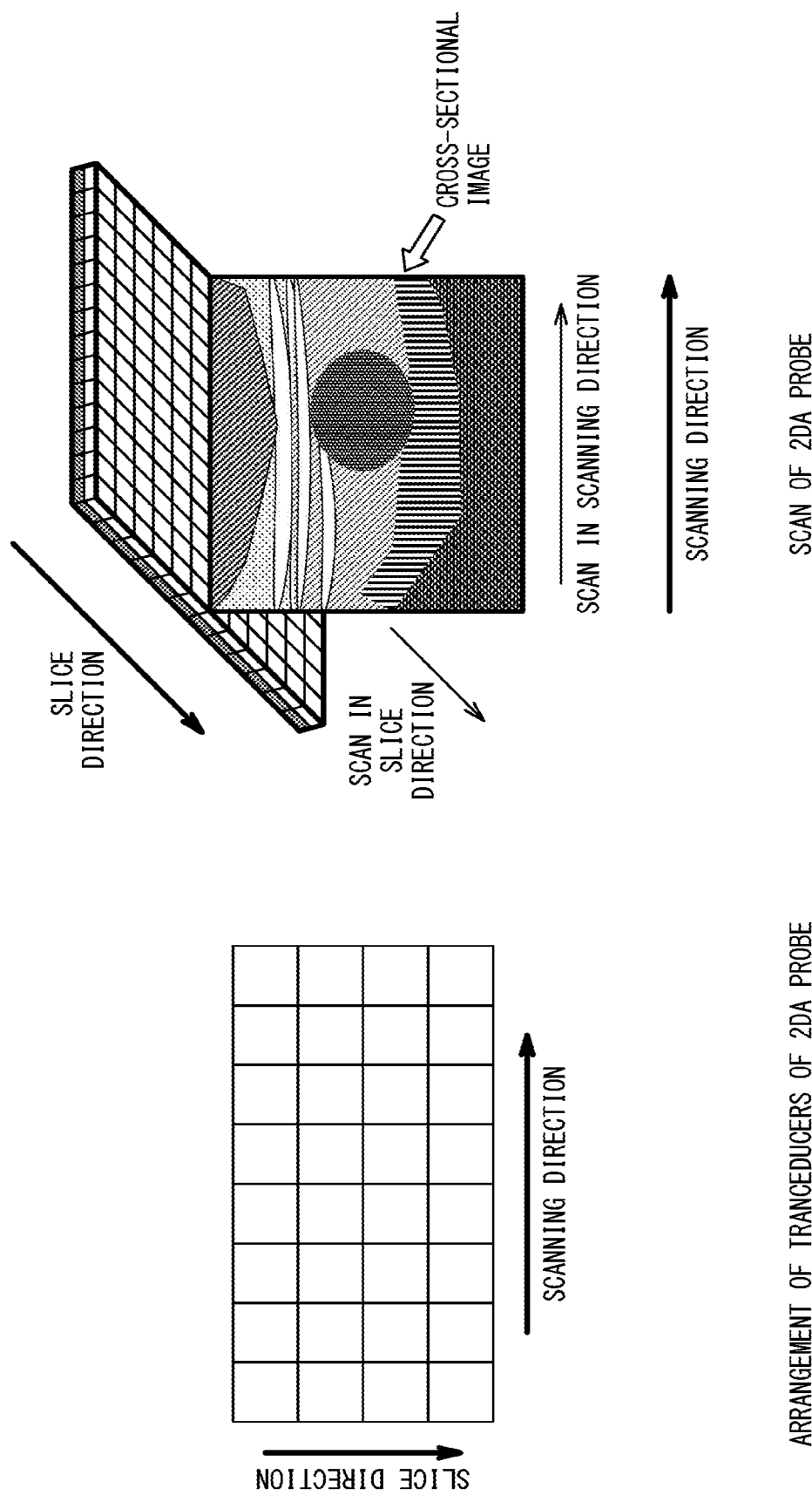
FIG. 9A is a schematic plan view illustrating arrangement of transducers of a 2DA probe.
FIG. 9B is a schematic perspective view illustrating a scan using a 2DA probe.

For instance, as to the target region P shown in FIG. 22, an ultrasonic probe is moved by a robot arm from the left side to the right side with respect to FIG. 22 so as to acquire ultrasonic reception signals as the first scan. Next, the ultrasonic probe is rotated by 90 degrees, and the ultrasonic probe is moved by the robot arm in the direction from the front to the back of the sheet of FIG. 22 so as to acquire ultrasonic reception signals as the second scan. The orientation of the ultrasonic probe with respect to the target region P is different between the first scan and the second scan. Incidentally, in the case of a 2DA probe, arrangement of its transducers is anisotropic as shown in FIG. 9, and thus a point-spread function of a beam formed by a 2DA probe is anisotropic. Here, beam width of an ultrasonic probe and a point-spread function of a beam formed by this ultrasonic probe are correlated to each other.

In the case of a 1DA probe, though its point-spread function (i.e., its beam width) can be narrowed on a scanning plane by electronic focusing, its focus in the slice direction is fixed by its acoustic lens, and thus, there is a large anisotropy in a point-spread function of a beam formed by the 1DA probe as shown in FIG. 15A to FIG. 15D. Anisotropy exists not only in the scanning direction and the slice direction of a beam but also in the depth direction. A larger spatial compound effect can be expected by coherently summing up data of a target region in which reception signals are acquired under conditions of different orientations of the ultrasonic probe and different incident angles of beams.

Further, each position of an ultrasonic probe and positional information of each beam, which are obtained from the arm sensor 111 attached to the robot arm 110, can be accurately recorded in the present embodiment. Accordingly, the spatial compound processing can be repeated on the same target region or the same target space by acquiring ultrasonic scanning data plural times. Furthermore, in order to further enhance image quality, relationship between point-spread functions of respective beams and cross-sectional directions to be displayed can be taken in account in the incoherent summation of beams in the spatial compound processing. For instance, weighted summation can be applied to the incoherent summation such that a larger weight is put on a beam with a smaller point-spread function in a displayed cross-sectional direction.

Additionally, the three-dimensional image processing function 216 in FIG. 2 can generate an MPR image and/or a three-dimensional image based on ultrasonic beam data with positional information. The incoherent summation can be performed by increasing a weight for a beam with comparatively high spatial resolution (i.e., small point-spread function) in an instructed direction of an MPR cross-section and/or a projection direction of a volume image. Additionally or alternatively, the incoherent summation can be performed by detecting an extending direction of a structure existing in a target region (e.g., a traveling direction of a blood vessel) and increasing a weight for a beam with comparatively high spatial resolution (i.e., small point-spread function) in the detected extending direction.

Further, in the case of depicting a parallel cross-section close to a body surface, weights of respective beams to be summed up can be changed according to an extending direction of each structure. For instance, in the case of a blood vessel, weighted summation is performed in such a manner that a larger weight is applied to a beam with a smaller point-spread function in the lateral direction of the blood vessel (i.e., in the direction perpendicular to the direction of blood flow). In this manner, blur of a vessel wall in the lateral direction can be reduced.

Moreover, in the case of performing the spatial compound processing, respective reception signals from the same region, which is a target the incoherent summation, can be incoherently summed up after being subjected to various types of calculation. For instance, respective reception signals may be incoherently summed up after being weighted according to intensity of respective reception signals. Additionally, the reception signal of the maximum value and at least one reception signal of a value close to the maximum value may be selected from plural reception signals acquired for the same region so as to be incoherently summed up. Additionally or alternatively, plural reception signals with high SNR may be selected from all the reception signals acquired for the same region so as to be incoherently summed up.

Further, respective reception signals acquired by transmission frequencies different from each other may be incoherently summed up. When a transmission frequency is higher, beam width is caused to be narrower to enhance resolution but attenuation in a deep part of an object is caused to be larger. Conversely, when a transmission frequency is lower, beam width is caused to be wider to reduce resolution but attenuation in a deep part of an object is caused to be smaller. Thus, an image of uniform quality can be generated by incoherently summing up respective reception signals acquired at different frequencies, such as a high frequency, a middle frequency, and a low frequency.

According to the ultrasonic diagnostic apparatus 1 of at least one of the above-described embodiments as described above, a three-dimensional image with high resolution and high image quality can be stably acquired over a wide scanning range.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a probe configured to be equipped with a plurality of transducers arranged two dimensionally in a first direction and a second direction perpendicular to the first direction and be able to perform a two-dimensional scan;
a moving device configured to support the probe and mechanically move the probe in the second direction;
a transmitting circuit configured to divide a transmission aperture of the probe into a plurality of partial transmission apertures and transmit respective ultrasonic signals from the plurality of partial transmission apertures, wherein a plurality of virtual point sound sources respectively corresponding to the plurality of partial transmission apertures are formed;

a receiving circuit configured to generate first reception signals for respective moving positions of the probe in the second direction, by performing receiving phase-compensation and summation processing on respective reflected signals received by the plurality of transducers at each of the respective moving positions; and processing circuitry configured to generate a second reception signal by performing moving aperture synthesis on the first reception signals generated for the respective moving positions of the probe based on positional information of the probe and generate image data from the second reception signal, wherein the first reception signals are a plurality of reception signals respectively corresponding to the plurality of partial transmission apertures;

the processing circuitry is configured to
  generate a plurality of processed signals by performing transmission aperture synthesis, the transmission aperture synthesis coherently summing up the first reception signals after correcting third respective delay amounts from the plurality of virtual point sound sources to an observation point in such a manner that the third respective delay amounts become substantially equal to each other, and
  generate the second reception signal from the plurality of processed signals subjected to the transmission aperture synthesis;

the receiving phase-compensation and summation processing performed by the receiving circuit is processing of generating each of the first reception signals by coherently summing up the respective reflected signals, wherein, before coherent summation of the respective reflected signals, first respective delay amounts from the observation point in three-dimensional space inside an object to the plurality of transducers are corrected to become substantially equal to each other; and the moving aperture synthesis is processing of generating the second reception signal by coherently summing up the first reception signals, wherein, when the probe is moved in the second direction, a beam formed by the probe is directed toward the observation point at each of moving positions of the probe by performing the two-dimensional scan by an electronic scan both in the first direction and the second direction, and before coherent summation of the first reception signal, second respective delay amounts from the observation point changed due to movement of the probe are corrected to become substantially equal for each of the moving positions of the probe.

2. The ultrasonic diagnostic apparatus according to claim 1,
  wherein the probe is configured in such a manner that number of the plurality of transducers arranged in the second direction is smaller than a number of the plurality of transducers arranged in the first direction.

3. The ultrasonic diagnostic apparatus according to claim 1,
  wherein the transmitting circuit is configured to divide the transmission aperture of the probe in the first direction into the plurality of partial transmission apertures; and
  the processing circuitry is configured to perform the transmission aperture synthesis in the first direction.

4. The ultrasonic diagnostic apparatus according to claim 1,
  wherein the transmitting circuit is configured to divide the transmission aperture of the probe in the second direction into the plurality of partial transmission apertures; and
  the processing circuitry is configured to perform the transmission aperture synthesis in the second direction.

5. The ultrasonic diagnostic apparatus according to claim 1,
  wherein the moving device is configured to be equipped with a robot arm; and
  the processing circuitry is configured to
    acquire probe information on a moving path of the probe controlled by the robot arm, the probe information including at least one of a position of the probe, velocity of the probe, and biological contact pressure of the probe, and
    perform the moving aperture synthesis on the first reception signals based on the probe information.

6. An ultrasonic diagnostic apparatus comprising:
a probe configured to be equipped with a plurality of transducers arranged two dimensionally in a first direction and a second direction perpendicular to the first direction and be able to perform a two-dimensional scan;

a moving device configured to support the probe and mechanically move the probe in the second direction;

a transmitting circuit configured to divide a transmission aperture of the probe into a plurality of partial transmission apertures and transmit respective ultrasonic signals from the plurality of partial transmission apertures, wherein a plurality of virtual point sound sources respectively corresponding to the plurality of partial transmission apertures are formed;

a receiving circuit configured to generate a plurality of first reception signals for respective moving positions of the probe, by performing receiving phase-compensation and summation processing on respective reflected signals received by the plurality of transducers at each of the respective moving positions; and processing circuitry configured to generate a second reception signal by performing moving aperture compound processing on the plurality of first reception signals generated for the respective moving positions of the probe based on positional information of the probe and generate image data from the second reception signal, wherein the plurality of first reception signals are a plurality of reception signals respectively corresponding to the plurality of partial transmission apertures;

the processing circuitry is configured to
  generate a plurality of processed signals by performing transmission aperture synthesis, the transmission aperture synthesis coherently summing up the plurality of first reception signals after correcting third respective delay amounts from the plurality of virtual point sound sources to an observation point in such a manner that the respective delay amounts become substantially equal to each other, and
  generate the second reception signal from the plurality of processed signals subjected to the transmission aperture synthesis, and the receiving phase-compensation and summation processing is processing of generating each of the plurality of first reception signals by coherently summing up the respective reflected signals, wherein, before coherent summation of the respective reflected signals, first respective delay amounts from the observation point in three-dimensional space inside an object to the plurality of transducers are corrected to become substantially equal to each other; and the moving aperture compound processing is processing of generating the second reception signal by incoherently summing up the plurality of first reception signals, wherein, when the probe is moved in the second direction, a beam formed by the probe is directed toward the observation point at each of moving positions of the probe by performing the two-dimensional by an electronic scan in the both the first direction and the second direction, and before incoherent summation of the plurality of first reception signals, second respective delay amounts from the observation point changed due to movement of the probe are corrected to become substantially equal for each of the moving positions of the probe.

7. The ultrasonic diagnostic apparatus according to claim 6, wherein the moving aperture compound processing is processing of generating the second reception signal by weighting the plurality of first reception signals and incoherently summing up the plurality of first reception signals subjected to weighting, and the weighting is set based on a beam width in a display direction of a three-dimensional image or in a cross-sectional direction of a three-dimensionally reconstructed MPR image to be displayed on a display.

8. The ultrasonic diagnostic apparatus according to claim 6, wherein the moving aperture compound processing is processing of generating the second reception signal by weighting the plurality of first reception signals and incoherently summing up the plurality of first reception signals subjected to weighting, and the weighting is set based on a beam width in an extending direction of a biological structure.

9. The ultrasonic diagnostic apparatus according to claim 6, wherein the moving device is configured to be equipped with a robot arm; and the processing circuitry is configured to
acquire probe information on a moving path of the probe controlled by the robot arm, the probe information including at least one of a position of the probe, velocity of the probe and biological contact pressure of the probe, and generate the second reception signal by performing the moving aperture synthesis on the plurality of first reception signals based on the probe information.

10. The ultrasonic diagnostic apparatus according to claim 9, wherein the processing circuitry is configured to
acquire a plurality of data from a same target region in directions different from each other, and perform the moving aperture compound processing by generating three-dimensional data from the plurality of data subjected to a predetermined calculation.

11. The ultrasonic diagnostic apparatus according to claim 10, wherein the predetermined calculation includes at least one of a weighting calculation based on signal intensity or a signal to noise ratio, a calculation based on a maximum value or a minimum value, and a calculation based on data acquired at frequencies different from each other.

* * * * *